United States Patent
Keenan et al.

(10) Patent No.: US 9,286,861 B2
(45) Date of Patent: Mar. 15, 2016

(54) SYSTEM AND METHOD FOR PROVIDING DIGITAL CONTENT

(75) Inventors: George Willard Keenan, South Jordan, UT (US); Jim Allen Colby, Highland, UT (US); Matthew B. Strong, Pleasant Grove, UT (US); Daniel Torgerson, Stansbury Park, UT (US); Garth Braithwaite, South Jordan, UT (US); Daniel Hatch, South Jordan, UT (US); Andrew Branch, South Jordan, UT (US); Randall Wright, South Jordan, UT (US); Sean Thayne, South Jordan, UT (US); Emerson Tyler Wright, South Jordan, UT (US); Jeremiah Stephenson, South Jordan, UT (US); Mark Miles, South Jordan, UT (US); Mac Sims, South Jordan, UT (US)

(73) Assignee: Provo Craft and Novelty, Inc., South Jordan, UT (US)

( * ) Notice: Subject to any disclaimer, the term of this patent is extended or adjusted under 35 U.S.C. 154(b) by 920 days.

(21) Appl. No.: 13/360,368

(22) Filed: Jan. 27, 2012

(65) Prior Publication Data

US 2012/0198545 A1 Aug. 2, 2012

Related U.S. Application Data

(60) Provisional application No. 61/437,461, filed on Jan. 28, 2011.

(51) Int. Cl.
*G06F 21/00* (2013.01)
*G06F 3/048* (2013.01)
*G05B 15/02* (2006.01)
*G09G 5/14* (2006.01)

(52) U.S. Cl.
CPC *G09G 5/14* (2013.01); *G06F 21/00* (2013.01); *G09G 2340/0464* (2013.01); *G09G 2358/00* (2013.01); *G09G 2370/022* (2013.01)

(58) Field of Classification Search
CPC ......... H04N 21/00; G06F 21/00; G06F 17/50; H04L 63/08; H04L 9/32; G05B 19/497–19/4099
See application file for complete search history.

(56) References Cited

U.S. PATENT DOCUMENTS

| | | | | |
|---|---|---|---|---|
| 5,548,649 | A * | 8/1996 | Jacobson | 713/153 |
| 6,463,352 | B1 * | 10/2002 | Tadokoro et al. | 700/169 |
| 7,346,930 | B1 * | 3/2008 | Boydstun | H04L 63/02 726/29 |
| 8,788,842 | B2 * | 7/2014 | Brouwer | H04L 9/0894 380/44 |
| 8,880,870 | B2 * | 11/2014 | Aizawa | 713/153 |
| 2007/0038581 | A1 * | 2/2007 | Keresman et al. | 705/64 |
| 2008/0263126 | A1 * | 10/2008 | Soman | 709/201 |
| 2009/0164785 | A1 * | 6/2009 | Metke et al. | 713/169 |
| 2009/0265769 | A1 * | 10/2009 | Lu et al. | 726/6 |
| 2010/0217719 | A1 * | 8/2010 | Olsen | B26D 5/00 705/318 |
| 2015/0121063 | A1 * | 4/2015 | Maller | H04L 63/0435 713/153 |

OTHER PUBLICATIONS c2.com, HMAC User Authentication, Apr. 24, 2009, pp. 1-3.*

* cited by examiner

*Primary Examiner* — Kaveh Abrishamkar
*Assistant Examiner* — James J Wilcox
(74) *Attorney, Agent, or Firm* — Honigman Miller Schwartz and Cohn LLP

(57) ABSTRACT

A method of electronically displaying glyphs. The method includes receiving a glyph spacing, moving a first glyph toward a second glyph along an axis, identifying an intersection of a first axis coordinate of the first glyph with a second axis coordinate of the second glyph, and moving at least one of the glyphs along the axis to separate the first and second axis coordinates of the respective first and second glyphs by the glyph spacing.

16 Claims, 19 Drawing Sheets

SYSTEM AND METHOD FOR PROVIDING DIGITAL CONTENT

RELATED APPLICATIONS

This Application claims the benefit of U.S. Provisional Application 61/437,461 filed on Jan. 28, 2011, which is entirely incorporated herein by reference.

FIELD OF THE INVENTION

The disclosure relates to systems and methods of delivering digital content for use on electronic cutting machines.

BACKGROUND

The scrapbook industry has provided consumers with various tools, such as mechanical cutting and embossing tools, as well as electronic cutting machines. These tools and machines may be used to create designs for personalizing books and journals, such as may be desired to memorialize events and memories. Scrap booking software may be used to create designs for cutting on the mechanical cutting tools. Generally, scrap booking software provides rudimentary design capabilities and/or is incapable of interacting with electronic cutting machines.

Software applications, such as rich internet applications (RIAs), which are web applications that generally have the features and functionality of traditional desktop applications, may include client and server portions for execution on a respective client computing device and a server computing device. RIAs typically form a stateful client application with a separate services layer on the backend. RIAs typically run in a web browser, or do not require software installation on a local machine, and run locally in a secure environment called a sandbox. A sandbox is generally a security mechanism for safely running programs. Sandboxes are often used to execute untested code, or non-trusted programs from unverified third-parties, suppliers and non-trusted users.

SUMMARY

One aspect of the disclosure provides a method of electronically displaying glyphs. The method includes receiving a glyph spacing, moving a first glyph toward a second glyph along an axis, identifying an intersection of a first axis coordinate of the first glyph with a second axis coordinate of the second glyph, and moving at least one of the glyphs along the axis to separate the first and second axis coordinates of the respective first and second glyphs by the glyph spacing.

Another aspect of the disclosure provides a method of electronically displaying glyphs that includes receiving first and second glyphs and determining a collision space between the first glyph and the second glyph by providing a bounding box around each glyph and identifying any intersections of the two bounding boxes. The collision space is defined at least in part by any intersecting space of the two bounding boxes. The method also includes separating the first and second glyphs by a separation distance between the respective bounding boxes along at least one axis when the collision space defines a size greater than zero.

In yet another aspect, a method of electronically displaying a cutting mat for an electronic cutting machine includes displaying a ruler along at least one axis of the cutting mat and resizing the ruler with respect to a zoom level of the mat. The ruler remains visible to a user irrespective of the zoom level.

In another aspect, a method of preparing digital content of use on an electronic cutting machine includes electronically displaying a glyph with cut paths, allowing the user to select and disable at least one cut path and cutting non-disabled cut paths of the glyph on the electronic cutting machine.

In yet another aspect, a method of communication with a server includes receiving a login request from an internet application, producing a hash-based message authentication code, producing a user session key, returning the hash-based message authentication code to the internet application, receiving an authenticate user request from the internet application, and returning the user session key to the internet application. The method further includes receiving a bridge communication from an electronic cutting machine bridge, returning a bridge identification to the electronic cutting machine bridge, receiving an authenticate bridge request from the electronic cutting machine bridge, and returning a user bridge key to the electronic cutting machine bridge.

Implementations of the disclosure may include one or more of the following features. In some implementations, at least one of the login request and the authenticate user request from the internet application is encrypted. The method may include decrypting at least one of the login request and the authenticate user request. In some implementations, at least one of the bridge communication and the authenticate bridge request from the electronic cutting machine bridge is encrypted. The method may include decrypting at least one of the bridge communication and the authenticate bridge request.

Another aspect of the disclosure provides an electronic cutting machine system that includes an internet application, a server in communication with the internet application, and an electronic cutting machine having a bridge in communication with the internet application and the server. The server receives a login request from an internet application and produces a hash-based message authentication code and a user session key. The server returns the hash-based message authentication code to the internet application. The server also receives an authenticate user request from the internet application and returns the user session key to the internet application. Moreover, the server receives a bridge communication from an electronic cutting machine bridge and returns a bridge identification to the electronic cutting machine bridge. The server receives an authenticate bridge request from the electronic cutting machine bridge and returns a user bridge key to the electronic cutting machine bridge. The internet application receives the user bridge key from the electronic cutting machine bridge.

In another aspect, a digital file for execution on an electronic cutting machine includes a descriptor file and at least one vector path file having cut path coordinate information executable on the electronic cutting machine. In some implementations, the descriptor file comprises extensible markup language. The descriptor file may include information for at least one of fonts, keyboard mappings, cutting instructions, and glyph groupings. In some examples, the descriptor file includes a font definition, a glyph definition, and a fill definition. The font definition may include a collection of glyphs. The descriptor file may include child glyph definitions (e.g., for composite parent glyphs).

The details of one or more implementations of the disclosure are set forth in the accompanying drawings and the description below. Other aspects, features, and advantages will be apparent from the description and drawings, and from the claims.

DESCRIPTION OF DRAWINGS

Like reference symbols in the various drawings indicate like elements.

DETAILED DESCRIPTION

The present disclosure provides design software that allows a user to create, design, review, and/or modify projects (e.g., scrap book designs). The projects can be realized by cutting the designs on an electronic cutting machine. Users may wish to create or add to scrap designs at his/her leisure in various locations and at various times. Design software that provides the user with design creation tools, content access, and/or portable access allows the user to maximize creative moments to create designs.

Figure 1:
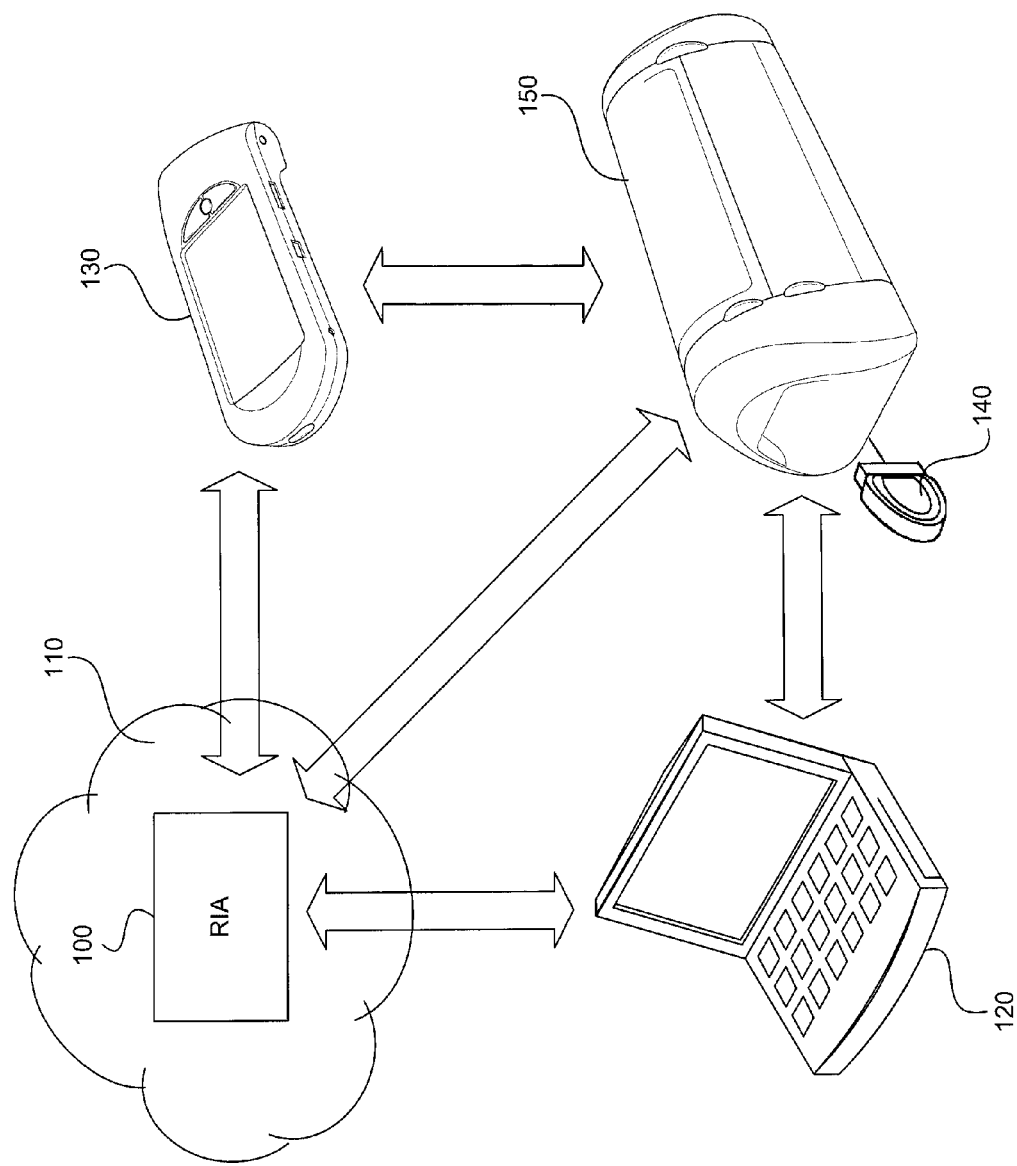
FIG. 1 is a schematic view of an electronic cutting system having design software interact with a computer, a hand-held controller, and/or an electronic cutting machine.
Figure 2:
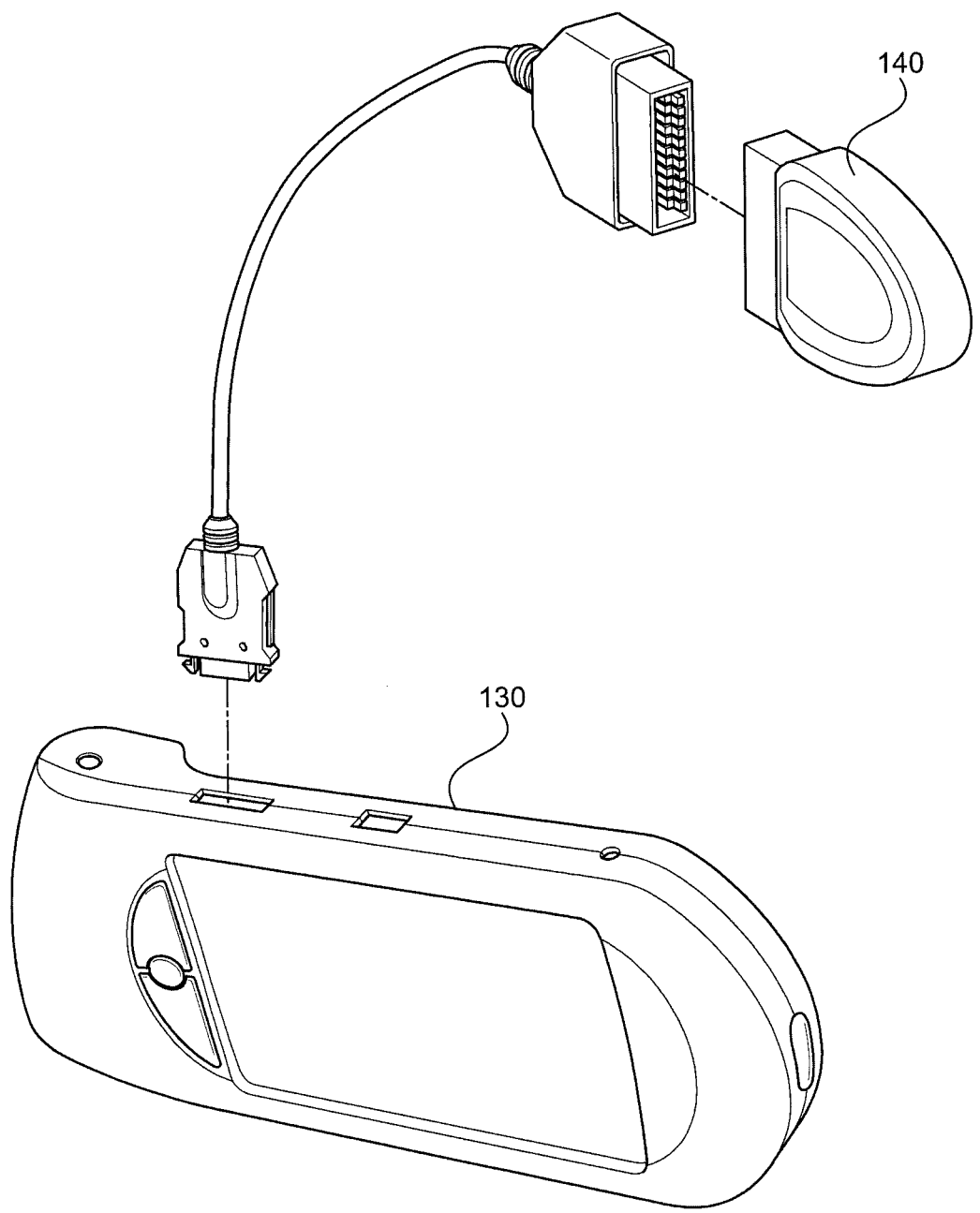
FIG. 2 is a perspective view of an exemplary hand-held controller establishing communication with an exemplary cartridge.

Referring to FIGS. 1 and 2, design software 100 may be used for creating and/or managing content as well as for interacting with an electronic cutting machine 150. The design software 100 may be stored in memory and executed on a processor of a computer 120, a hand-held controller 130, and/or the electronic cutting machine 150, each of which may provide a platform to store, use, and review digital content. In addition, the design software 100 may provide interaction with other design systems and/or community programs (e.g., uploading-publishing to blogs and other community websites, as well as downloading designs from the same). The design software 100 may interface with an electronic cutting machine 150 to realize designs by cutting out the constituent components of the designs, such as paper cutouts. Additionally, the digital content accessed in the design software 100 to create the designs can be compatible with the electronic cutting machine 150, and other devices, such as printers. In some implementations, the design software 100 provides access to digital content in a secure manner so as to allow for unfettered use by the owner while providing security against unauthorized duplication.

In some implementations, the design software 100 executes on a cloud client 110 of a cloud computing scheme. Cloud computing allows users to use applications without installation and provides access to their personal files at any computer or computing device with internet access. In general, cloud computing is virtualized third-party hosting, for example, where a user's server runs inside a virtual container which can be moved from one physical server to another without interruption of service. Such a container is also capable of spanning multiple physical machines, giving it potentially limitless resources. This allows for much more efficient computing by centralizing storage, memory, processing and bandwidth. In some implementations, the design software executes on a cloud client 110 that relies on cloud computing for application delivery, or is specifically designed for delivery of cloud services (e.g., content, design applications, etc.). The design software 100 may be a rich internet application (RIA) received through cloud computing. The design software 100 may provide design creation tools and capabilities. Moreover, the user may receive design applications and/or content on demand to the user's own computer 120 (e.g., laptop) or other computing devices, such as a hand held controller 130 of the electronic cutting machine 150, by accessing a subscription service. The digital content can be delivered by the cloud client 110 (e.g., a web server executing in a virtual container).

In some implementations, the user may access content (e.g., glyphs) for use with the design software 100 through a cartridge 140, which may be in communication with the electronic cutting machine 150, as shown in FIG. 1, or the hand held controller 130, as shown in FIG. 2. The cartridge 140 may store content in memory of the cartridge and/or content associated with the cartridge 140 may be stored on a cloud client 110 accessible by the design software 100. The user may access and design with content not otherwise owned by the user; however, when the user executes a cutting operation on the electronic cutting machine 100, the user may be required to verify ownership of any content used in a design to be cut. Ownership of content can be verified by establishing communication of any respective cartridges 140 with the design software 100 (e.g., via the hand held controller 130) and/or the electronic cutting machine 150. Moreover, the user may be prompted to purchase any content not owned by the user before allowing execution of the cutting operation on the electronic cutting machine 150.

The user may access the design software 100 as a rich internet application (RIA), create designs or projects using content provided by the design software, and save the designs or projects for later execution on an electronic cutting machine 150. The user may establish communication between the electronic cutting machine 150 and the design software 100 for executing cutting operations by wireless or electrical (e.g., Ethernet) connections to a computer 120 or other computing device 130 (e.g., hand-held device) running the design software 100 or to a network having internet connectivity for accessing the design software 100. While in communication with or executing the design software 100, the electronic cutting machine 150 may access information, such as machine type, cartridge type or content specific information from a cloud source (e.g., data storage in the cloud). Moreover, the design software 100 may access information from the electronic cutting machine 150 (such as make, model, owner information, stored content, etc.).

In some implementations, the design software 100 receives credit card information from the user to authenticate the user's log in. The design software 100 may require connection or communication with the controller device 130 of the electronic cutting machine 150 to authentication of the user. In some examples, the design software 100 tracks the browsing and usage of content for creating designs and delivers content (e.g., visually) to the user based on past usage of similar content (e.g., by category, keyword, etc.) and/or statistical analysis. Content may also be delivered to the user based on promotional activities or incentives.

Figure 3:
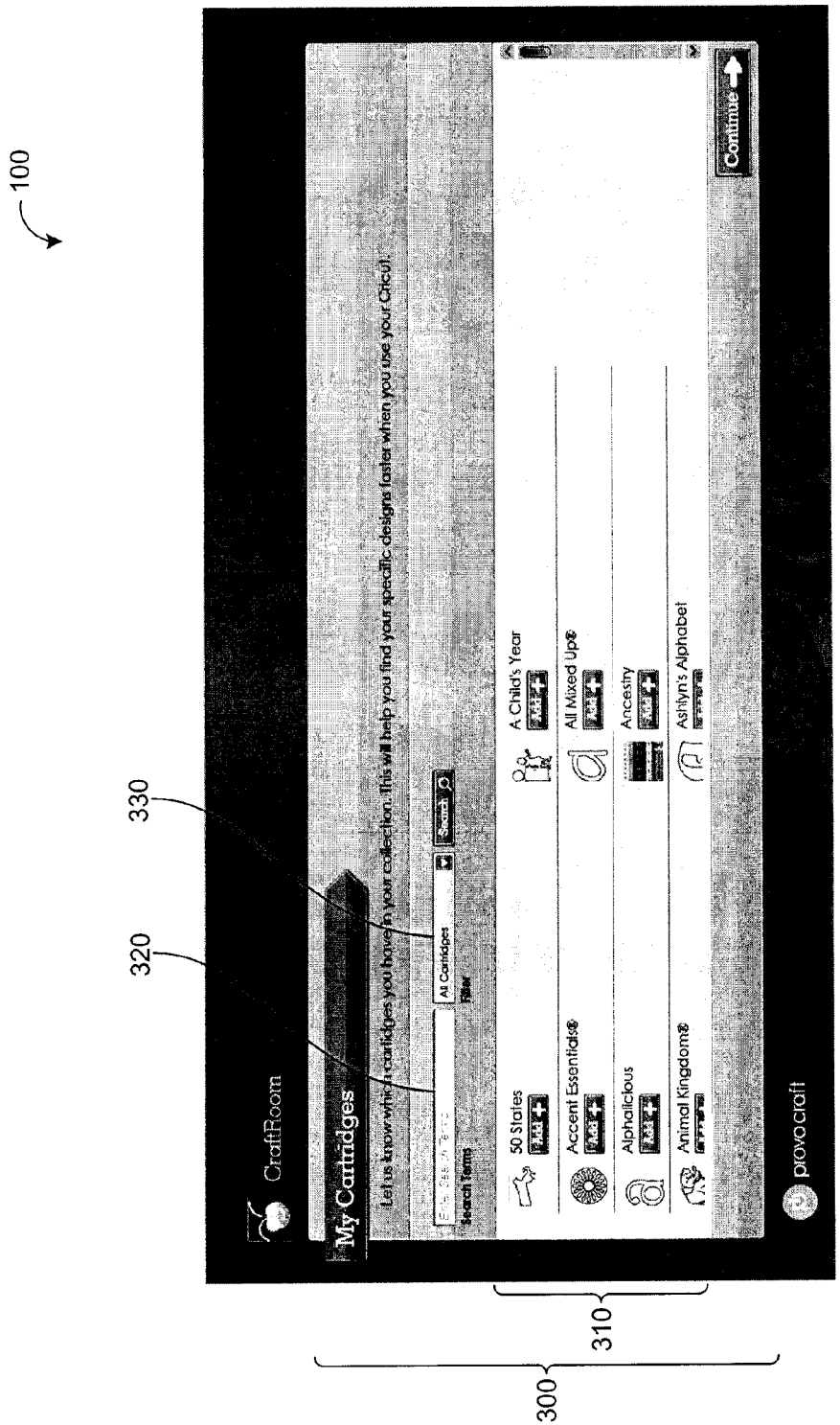
FIG. 3 is a schematic view of an exemplary cartridges view of design software for creating and/or managing content as well as for interacting with an electronic cutting machine.

Referring to FIG. 3, in some implementations, the design software 100 includes a cartridge view 300 that allows the user to locate, browse, and/or access cartridges 140 (e.g., to view content). In the example shown, the cartridge view 300 provides a list view 310 of cartridges 140 accessible by the user. The cartridge view 300 may include a search text box 310 that can receive search terms for locating cartridges according to the received search term(s) (e.g., by querying a database). In the example shown, the cartridge view 300 includes a filter drop down combo box 330 that can provide a list of cartridge categories. Once a cartridge category has been selected, the design software 100 can provide a collection of cartridges 140 associated with the selected cartridge category in the list view 310 (e.g., by querying a database).

Figure 4:
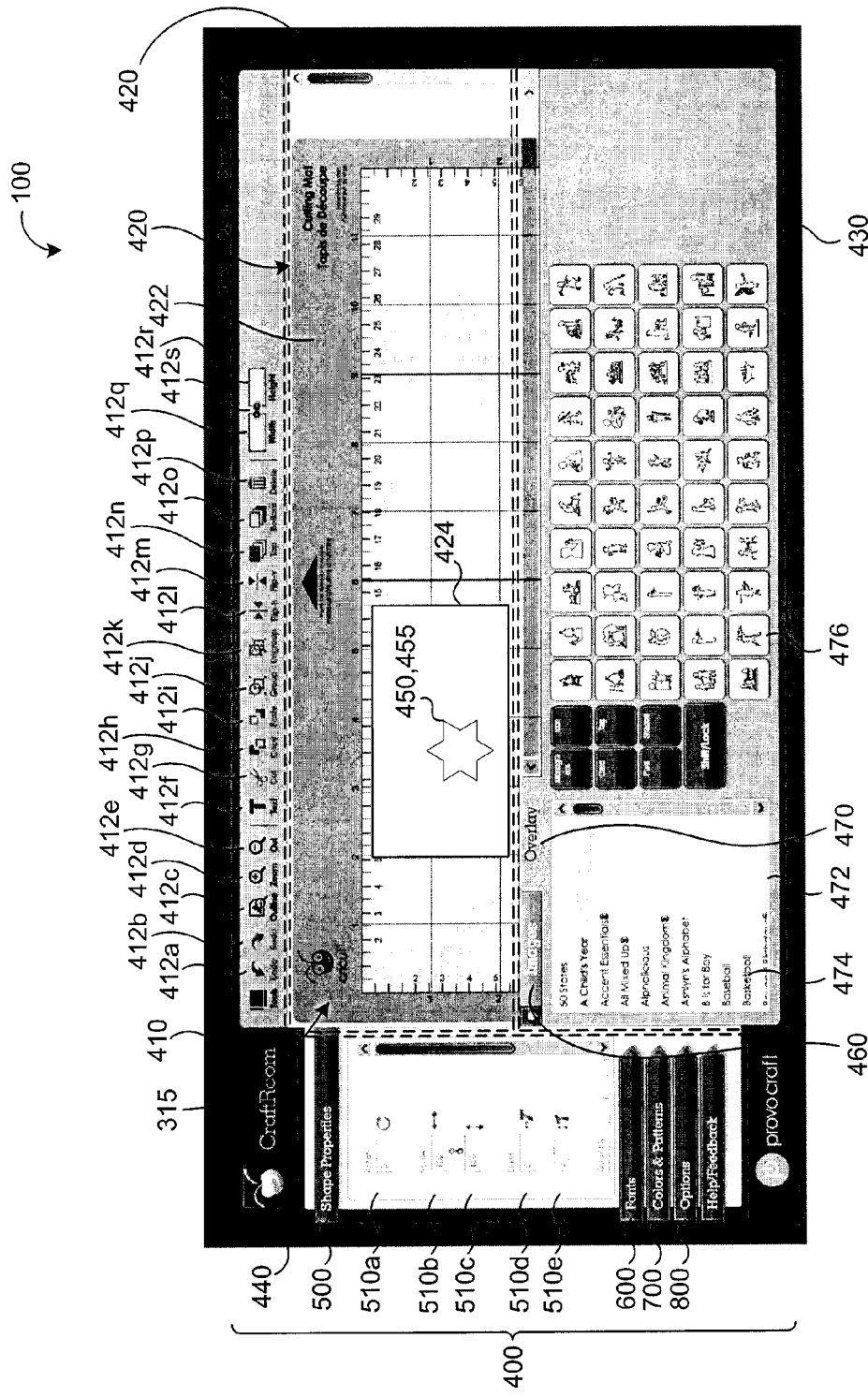
FIG. 4 is a schematic view of an exemplary design view of design software for creating and/or managing content as well as for interacting with an electronic cutting machine.

Referring to FIG. 4, in some implementations, the design software 100 includes a design view 400 for creating and editing projects 315. In the example shown in FIG. 4, the design view 400 includes a toolbar 410, a virtual mat view 420, and a content portion 430 (e.g., navigation bar or view). The toolbar 410 includes one or more commands 412 for editing, manipulating, or otherwise interacting with a project 315. For one or more (or all) of the commands, the design software 100 may provide visual feedback of the executed command by indicating which command was selected and by showing a selected design object 450 change or alter as a result of the executed command. Moreover, the design software 100 may show on the virtual mat 422 how much available paper has be used or occupied as a result of the executed command.

As used herein, the term "design object" refers to something that is or can be selected by the user for manipulation, such as by executing a user initiated command. A design object 450 may be a glyph 455 or part of a glyph 455 (e.g., a subset of a glyph). For example, a command can be executed on a region of a multi region glyph 455. An exemplary single region glyph 455 is a circle, while an exemplary multi region glyph 455 is a figure-eight. A glyph 455 having multiple closed vector loops will have multiple regions defined by those vector loops. Each of these regions can be selected by the user. For example, when executing a copy command, the user first selects the glyph 455 and then a region of the glyph 455 that is to be copied.

A design object 450 may be a single glyph project as an entire project 315. For example, a project 315 may include data for orientation and size, but as long as only one glyph is in the job or project 315, then the project 315 may be considered single glyph. A design object 450 may be a multi-glyph project 315 as an entire project 315 (e.g., a project having multiple glyphs). In some examples, a design object 450 is a single glyph of a multi-glyph project 315. For example, the user can select a single glyph 455 from among multiple glyphs 455 in a project 315 and execute a command on the selected glyph 455. Moreover, in some examples, the user can select multiple glyphs 455 of a multi-glyph project 315 (e.g., a subset of a project 315) as a design object 450 and execute a command on the selected glyph 455. The design object 450 may be a single exploded layer, which can be a layer that is no longer part of a composite image. A composite image that has been exploded into multiple layers may have each layer treated as an individual glyph 455 or design object 450. In additional examples, the design object 450 can be a single layer of a composite image (e.g., a paletted or non-exploded image).

Examples of toolbar commands 412 include undo 412$a$ (e.g., undo x number of commands) and redo 412$b$ (e.g., redo or re-execute n number of commands). The user may execute the undo command 412$a$ to undo or cancel one or more previous actions or commands 412. The actions or commands 412 may be undone in reverse chronology. The user may also redo or re-execute actions or commands that have been undone by executing the redo command 412$b$. In some examples, the toolbar 410 includes a clear all command (not shown) that clears the entire job (e.g., from memory and/or the virtual matt 422). The design software 100 may indicate that the clear all command has been selected or executed and may offer a confirmation screen to confirm the user's action to clear the entire job.

The toolbar 410 may include toolbar commands for viewing the project 315 in different ways. Exemplary viewing commands may include outline 412$c$ (e.g., to provide an outline cut view of the project), zoom in 412$d$ (e.g., zoom in on a portion of the virtual mat), and zoom out 412$e$ (e.g., zoom out on a portion of the virtual mat). A type command 412$f$ may be sued to create a text field for typing characters or strings. Additional examples of toolbar commands may include cut 412$g$, copy 412$h$, paste 412$i$, group 412$j$, ungroup 412$k$, flip horizontal 412$l$ (e.g., flip a selected design object about a y-axis), flip vertical 412$m$ (e.g., flip a selected design object about an x-axis), move a selected layer to top 412$n$, move a selected layer to bottom 412$o$, and delete 412$p$. In some examples the toolbar 410 includes height 412$q$ (e.g., set a height of a selected design object), width 412$r$ (e.g., set a width of a selected design object), and scale locking 412$s$ (e.g., lock a height to width relationship). In some examples, the user may customize the toolbar 410 by adding, removing, and/or arranging commands on the toolbar 410.

The virtual mat view 420 includes a virtual mat 422, which may include at least one virtual paper 424 (representing actual paper for cutting on the electronic cutting machine 150). The user may place design objects 450 (e.g., glyphs) on the virtual mat 422 and/or virtual paper 424 for creating and/or editing a project 315. The virtual mat view 420 any include a cut command for sending the project 315 to an electronic cutting machine 150 in communication with the design software for execution of a cutting operation. The virtual mat view 420 may also include a panning command (e.g., up, down, left, right arrows) for moving a view of the virtual mat 422 in the virtual mat view 420.

Figure 5:
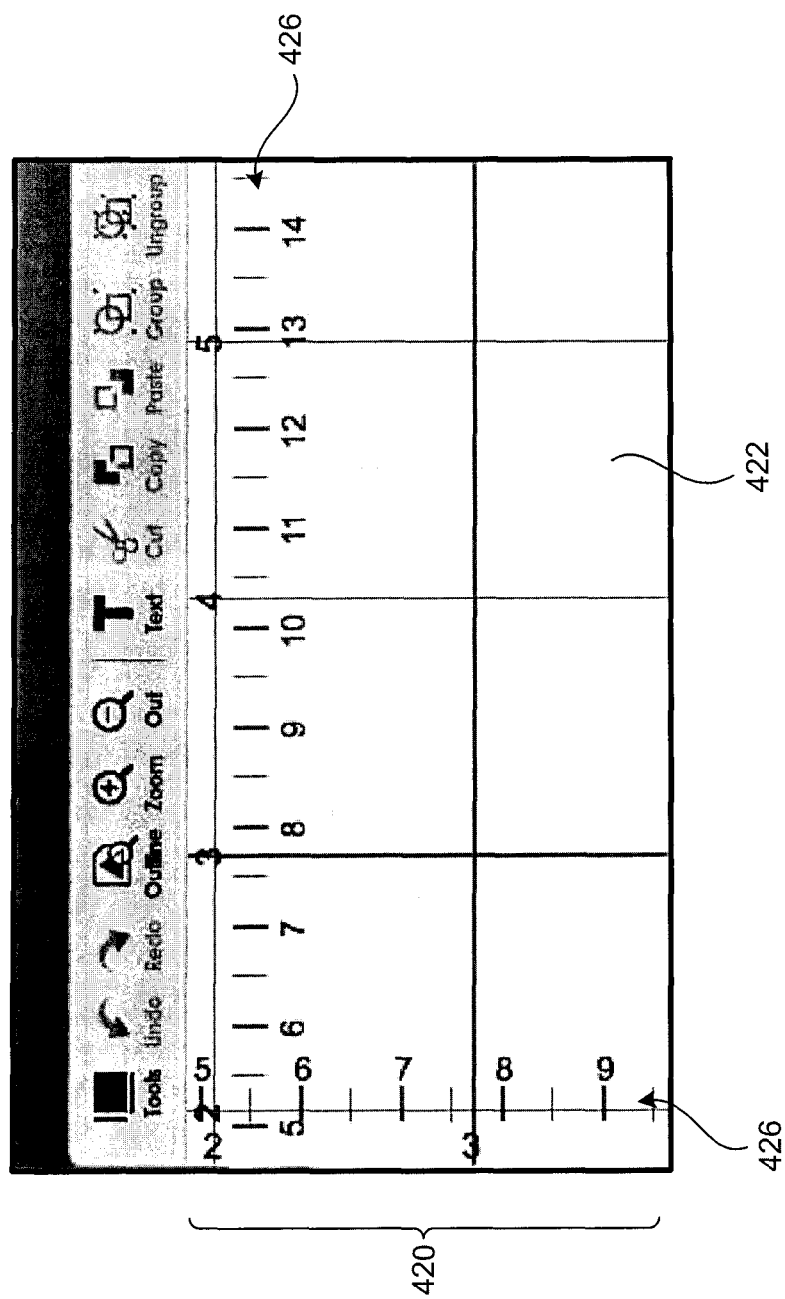
FIG. 5 is a schematic view of an exemplary virtual mat having a floating ruler.

Referring to FIG. 5, in some implementations, the virtual mat view 420 includes a floating ruler 426 (e.g., along one or more edges (X and/or Y) of the virtual mat 422. As the user zooms in or out on the virtual mat 422, the floating ruler adjusts correspondingly to provide the user with actual or relative size dimensions of the viewed mat space on the virtual mat 422. An actual mat used on the electronic cutting machine 150 may have a dimensions printed or applied thereto for alignment and sizing of designs. The virtual mat 422 may include a replicated dimensioned portion along one or more edges; however, as the user zooms into a specific region of the virtual mat 422, the edge dimensions may no longer be viewable. The floating ruler 426 can provide these dimensions and optionally other dimensions, such as relative dimensions with respect to the virtual mat and/or other objects. The floating ruler 426 may remain visible to the user irrespective of a zoom level on the virtual mat 422.

Referring again to FIG. 4, in some implementations, the design view 400 includes a command menu 440 (e.g., accordion menu) having one or more command palettes (e.g., tabs). One or more of the commands of the command menu 440 may be executable on one or more design objects 450 in the design view 400. In the example shown in FIG. 4, the command menu 440 includes a shapes palette 500, a fonts palette 600, a colors palette 700, and an options palette 800.

The shapes palette 500 may include transformation commands, such as a rotation command 510a for setting a rotation of a selected design object 450 with respect to an axis, such as an X axis. For example, the design software 100 may allow a user to select a design object 450 and set an orientation of the design object 450 (e.g., landscape or portrait, or change the orientation of the object by an angle, such as 0°, 45°, 90°, 180°, etc.). Moreover, the user may select design objects 450 (e.g., glyphs 455) and all respective nested attributes (i.e., patterns from a palette) and change their orientation. If a selected design object 450 has already been rotated, the rotation command 510a is added to the existing orientation of that design object 450. The design software 100 can provide visual feedback of the executed command by showing the design object 450 change orientation with respect to a previous orientation and/or by showing how much available paper 424 has be used or occupied as a result of the executed command. Other transformation commands may include scale-X 510b (e.g., to set a scaling factor along the X axis of the virtual mat 422 for sizing a selected design object 450), and scale-Y 510c (e.g., to set a scaling factor along a Y axis of the virtual mat 422 for sizing a selected design object 450).

The shapes palette 500 may include slant-X 510d (e.g., for setting a character slant with respect to an x axis) and slant-Y 510e (e.g., for setting a character slant with respect to an y axis).

Figure 6:
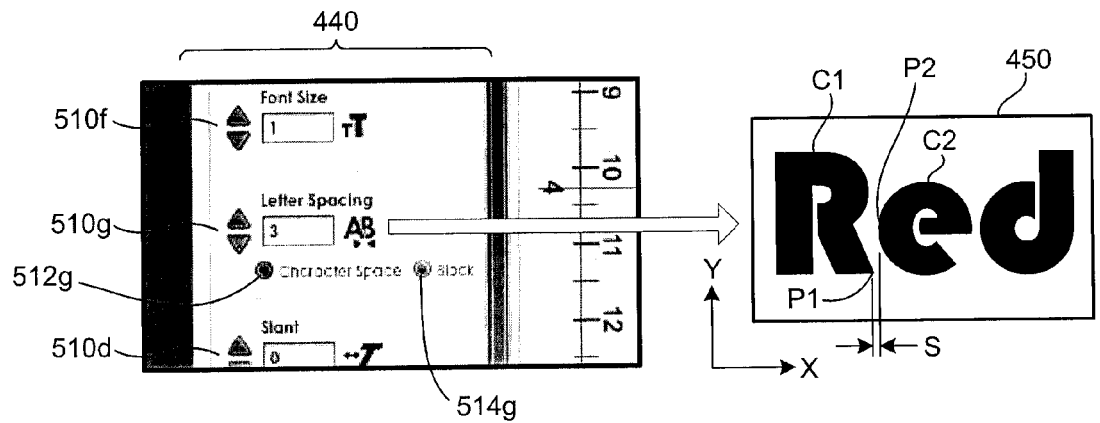
FIG. 6 is a schematic view of an exemplary letting spacing control adjusting a letter spacing between adjacent letters of a text design object.

Referring to FIG. 6, in some implementations, the command menu 440 includes a font size command 510f for adjusting a font size of text and a letter spacing command 510g (e.g., kerning) for setting a spacing S between adjacent letters or glyphs 455 of a selected design object 450. The user may select a character spacing option 512g or a block spacing option 514g to have the letter spacing command 510g determine a character spacing S based on a character path intersection offset or a character perimeter box offset, respectively.

For executing the letter spacing command 510g using the character spacing option 512g, the letter spacing command 510g can execute a routine for determining a distance between visible edges of adjacent first and second characters C1, C2. In some implementations, the spacing command 510g identifies a point of intersection between any path of the first character C1 and any path of the adjacent second character C2 along an X-axis. For example, an intersection between two adjacent characters C1, C2 can be identified as a location along the X-axis where an X-coordinate of a first point P1 of a path of the first character C1 is equal to an X-coordinate of a second point P2 of a path of the second character C2 as the two characters C1, C2 are moved toward each other along the X-axis. The character spacing S can be defined as a distance along the x-axis between the first and second points P1, P2. A character path can be defined as stroke path of the character (letter) or a Bezier curve of the character. In additional examples, first and second characters C1, C2 can be moved toward each other along the X-axis until a path of the first character C1 intersects a path of the second character C2. The letter spacing command 510g can identify corresponding first and second points P1, P2 on the intersecting paths of the first and second characters C1, C2 at the location of intersection. The letter spacing command 510g may then set a spacing S between the first and second points P1, P2 (e.g., along the X-axis), thus setting a spacing between the corresponding characters C1, C2. In some examples, the letter spacing command 510g can be broadened to a design object spacing command that determines a spacing between adjacent design objects 450, using the same principles.

In some examples, each character has an associated character box surrounding or circumscribing the character. The letter spacing command 510g positions first and second adjacent characters to have a user specified distance between edges of their corresponding character boxes (e.g., along the X-axis).

A method of determining the character spacing S between the first and second characters C1, C2 (or a design object spacing between first and second adjacent design objects 450) may include receiving a list of elements (e.g., characters C1, C2 or design objects 450) and determining which elements are touching or colliding (e.g., positioned or arranged on the virtual mat 422, such that the two elements intersect at least one point). The list of elements may be a multi-dimensional array. In some examples, the method includes iterating through the list of elements and comparing each element against all of the other elements in the list of elements. For each comparison, the method may include determining a collision space (e.g., a rectangle) between the two elements (e.g., design objects 450) by instantiating bounding boxes around the two elements in a common coordinate space and finding an intersection of the two bounding boxes, if any. The bounding boxes may be rectangular, circular, polyhedron or any other suitable shape (e.g., a perimeter path). If the collision space has a zero size, then the method includes returning that the elements do not touch. If the collision space (or an intersection region of the two bounding boxes) has a size greater than zero, then the method may include recording that the elements intersect and/or determining a minimum spacing between the two elements.

Instantiating a bounding box may include identifying sub-elements of an element, determining a bounding region for each sub-element (e.g., a rectangle or other suitable shape circumscribing the sub-element), and unionizing or combining the sub-element bounding regions or determining an element bounding region that bounds or circumscribes the sub-element bounding regions (e.g., a rectangular, circular, polyhedron or other shaped boundary around the element). In examples where the element or a sub-element has been rotated in the coordinate space, the method may include determining a bounding region that does not include any padding or non-element space around the rotated element or sub-element.

In some implementations, the method includes positioning the compared elements to have a spacing S between their respective bounding boxes along at least one of the X and Y axes. For example, an X coordinate of one of the two elements can be incremented by the spacing S.

Figure 7:
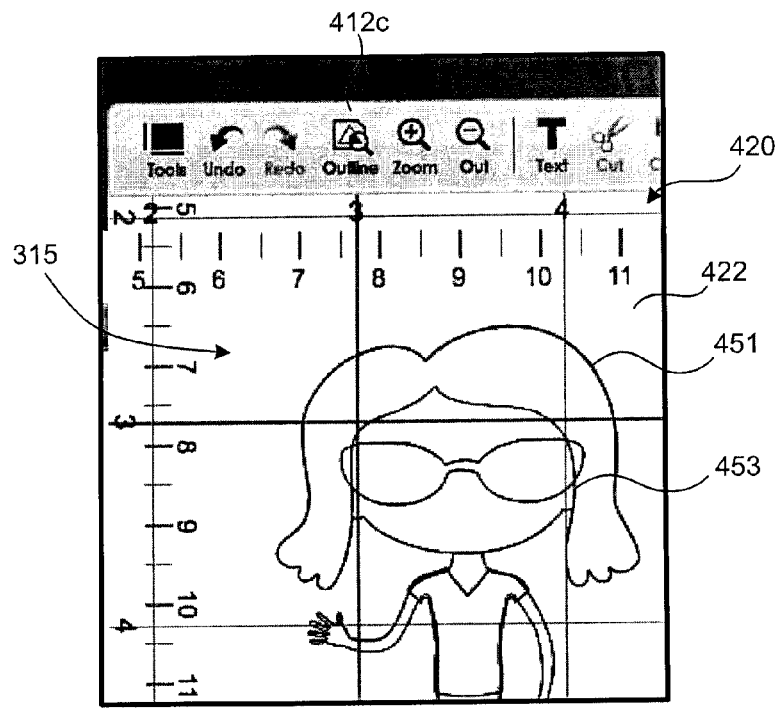
FIG. 7 is a schematic view of an exemplary outline control providing an outline cut path for a selected design object.
Figure 8:
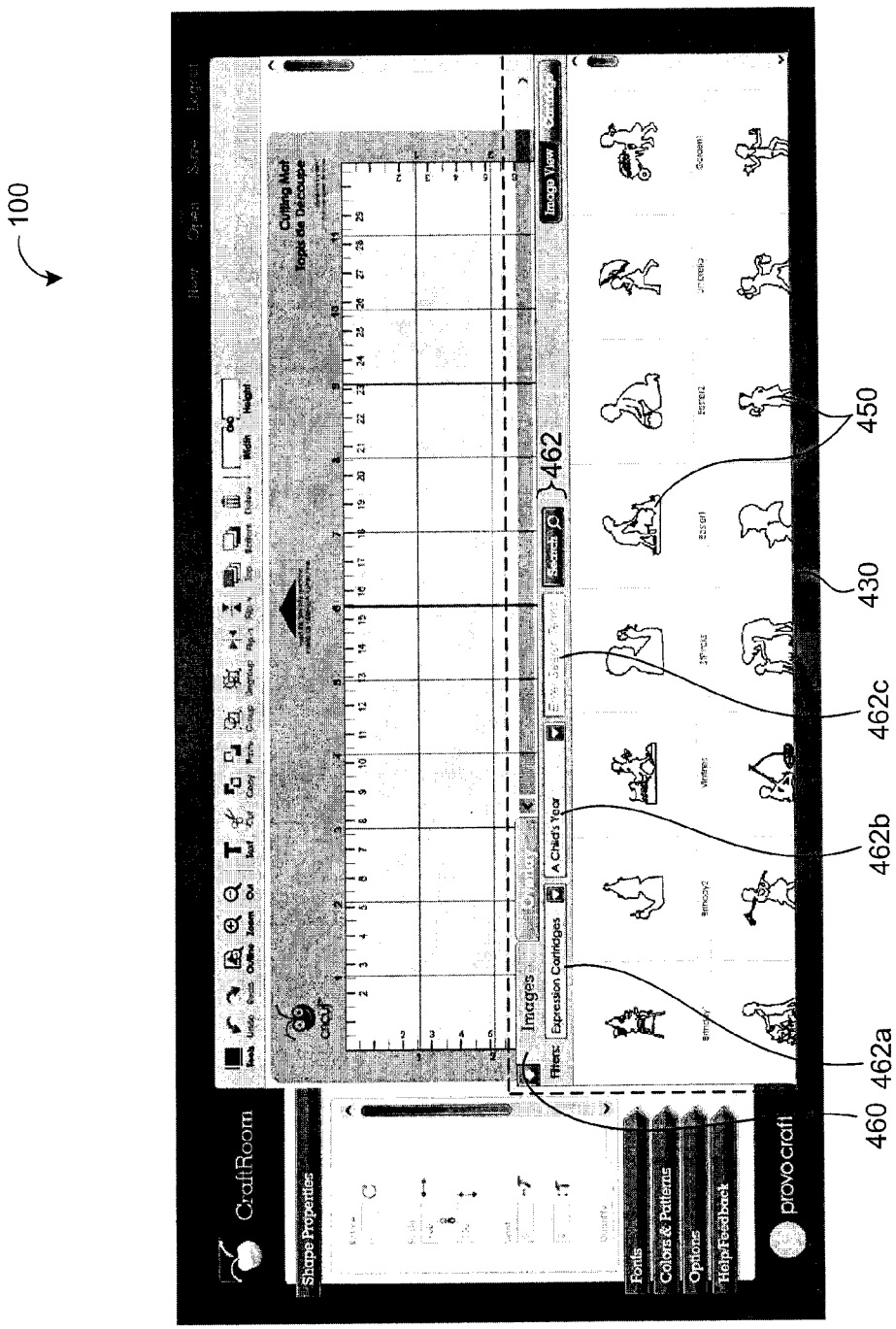
FIG. 8 is a schematic view of an exemplary design view of design software having an images content portion.
Figure 9:
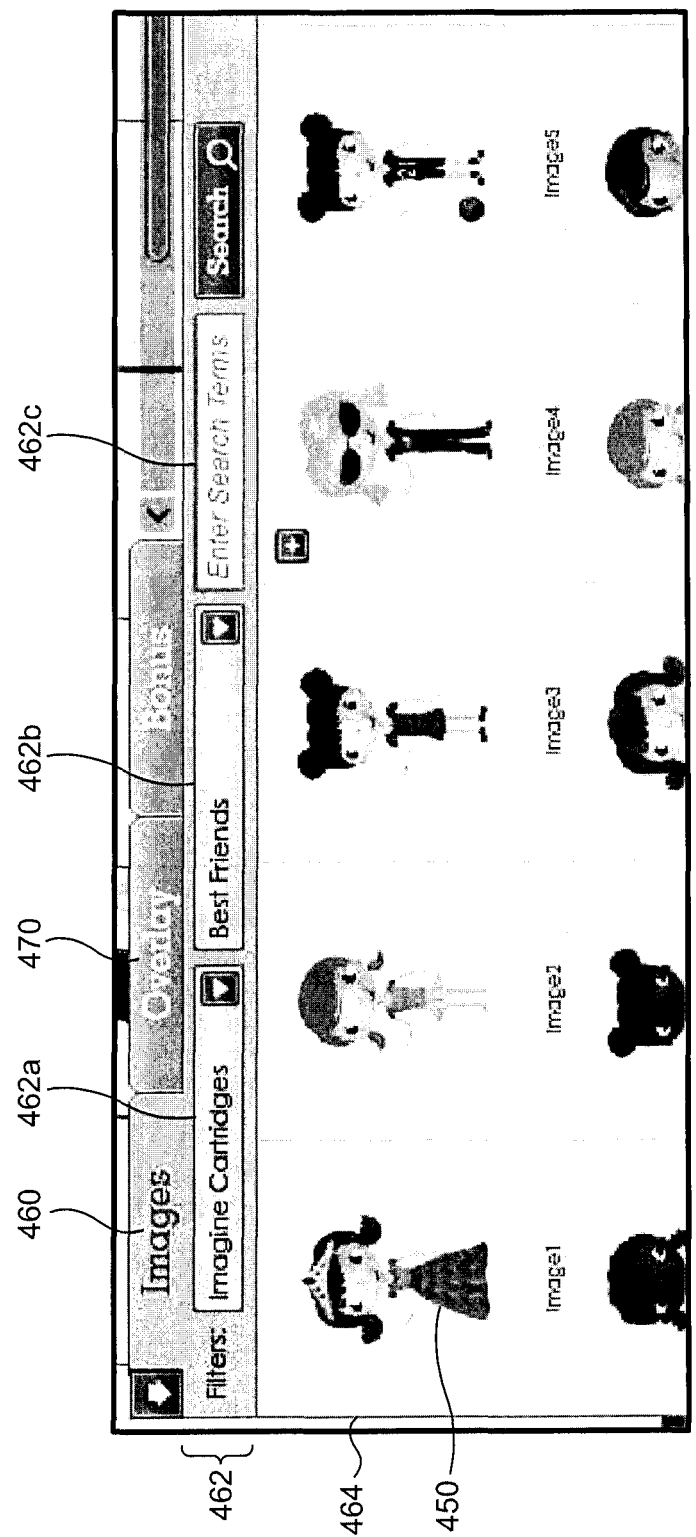
FIG. 9 is a schematic view of an exemplary images content portion of a design view.
Figure 10:
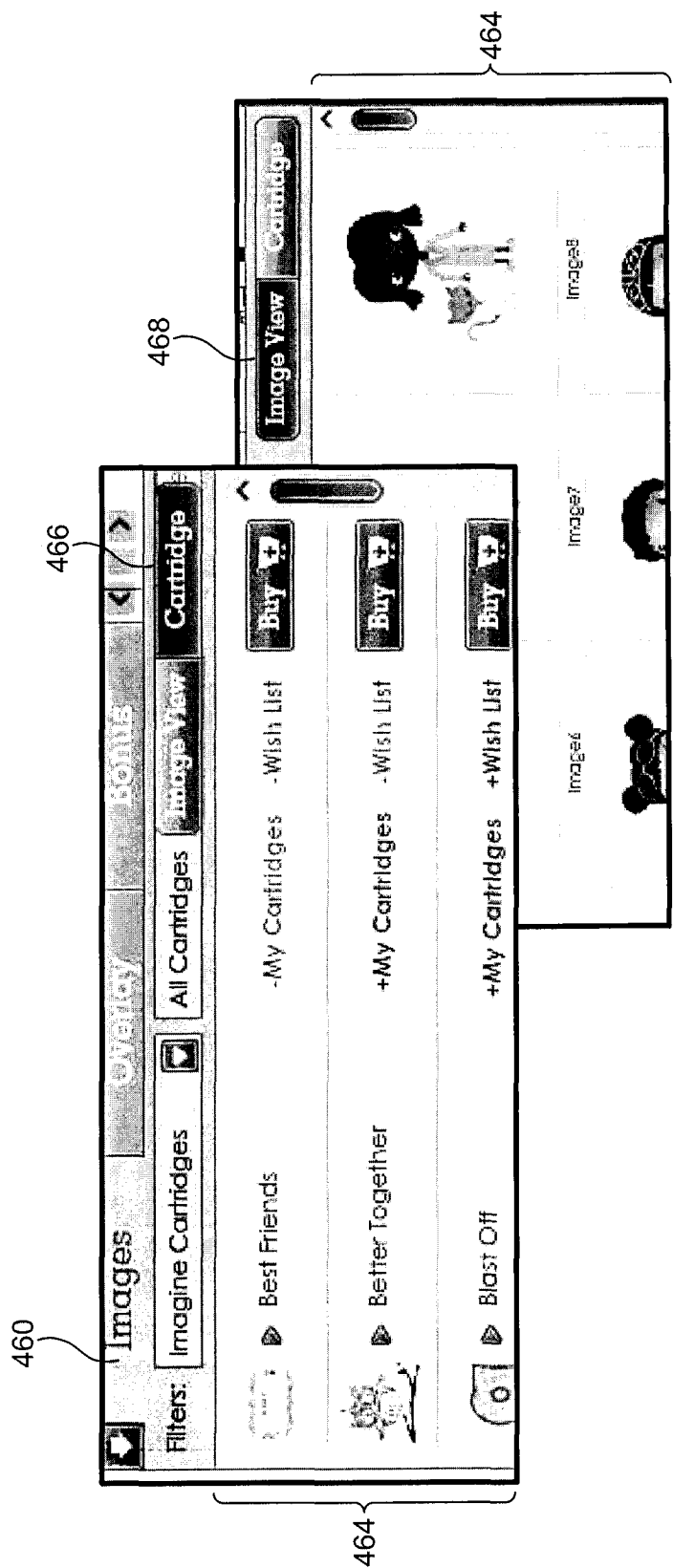
FIG. 10 is a schematic view of an exemplary cartridge and image views of an images content portion of a design view.

Referring to FIG. 7, the outline command 412c may show the user what the project 315 will look like after cut on the electronic cutting machine 150. For example, the outline command 412c can provide a view of the project 315 on the virtual mat 422 as if cut on the electronic cutting machine 150. In one example, the outline command 412c determines and displays a perimeter, outline, or primary cutting path 451 of the project 315 and displays it on the virtual mat 422. The user may execute a hide contour command on a selected design object 450 to hide or remove one or more object paths or cut paths 453. When the electronic cutting machine 150 cuts the design object 450, the hidden or removed cut paths 453 are not cut.

Referring to FIGS. 4 and 8-10, in some implementations, the content view portion 430 of the design view 400 includes an images tab view 460 and an overlay tab view 470. In the example shown in FIG. 4, the overlay tab view 470 provides a list view 472 of overlay categories or cartridges and a corresponding collection of overlays 476 for selected overlay category 474 in the list view 472. In the example shown in FIG. 8, the images tab view 460 includes a search bar 462 having a cartridge type 462a for viewing content by one or more types of cartridges, a cartridge filter 462b for viewing content of one or more selected cartridges or categories, and a search string field 462c for searching relevant content by a received search string. The search may be a key word search on cartridge names, tags, and/or other fields. The content may be glyphs 450 displayed in a content results portion 464 and which can be added (e.g., via drag-and-drop) to a project 315 in the virtual mat view 420. The content results portion 464 can be a list view, table or grid, tree, or other suitable control for displaying a collection of items. In the example shown in FIG. 9, the content view portion 430 allows the user to toggle between a cartridge view via a cartridges option 466 and an images view via an image option 468. With the cartridges option 466 selected, the content results portion 464 displays cartridges according to an executed search criteria set in the search bar 462. In some examples, the content results portion 464 displays the cartridges in a tree view or tree-grid view that allows the user to expand a tree node of a selected cartridge to view content, properties, or features of the cartridge. With the images option 468 selected, the content results portion 464 displays images or glyphs according to an executed search criteria set in the search bar 462.

Figure 11A:
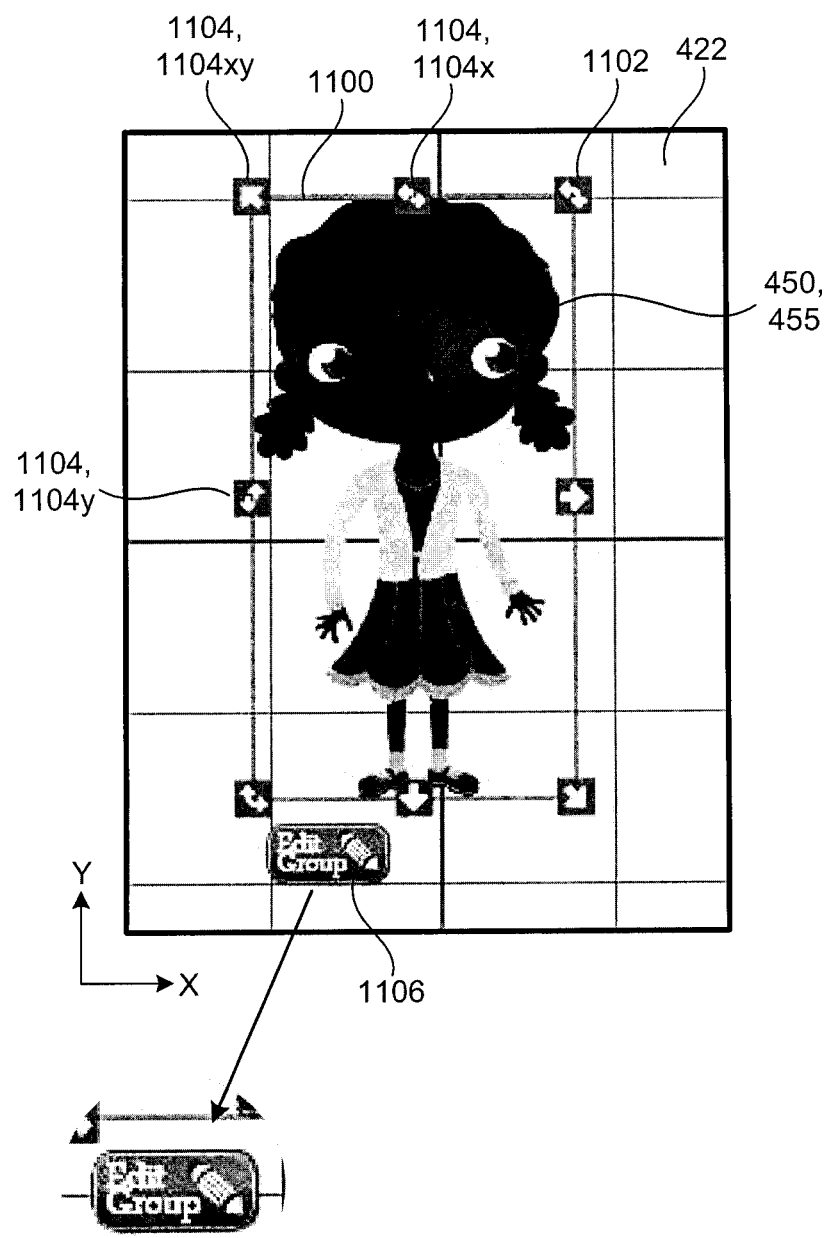
FIG. 11A is a schematic view of a selected grouped or composite image having an edit box with edit handles.
Figure 11B:
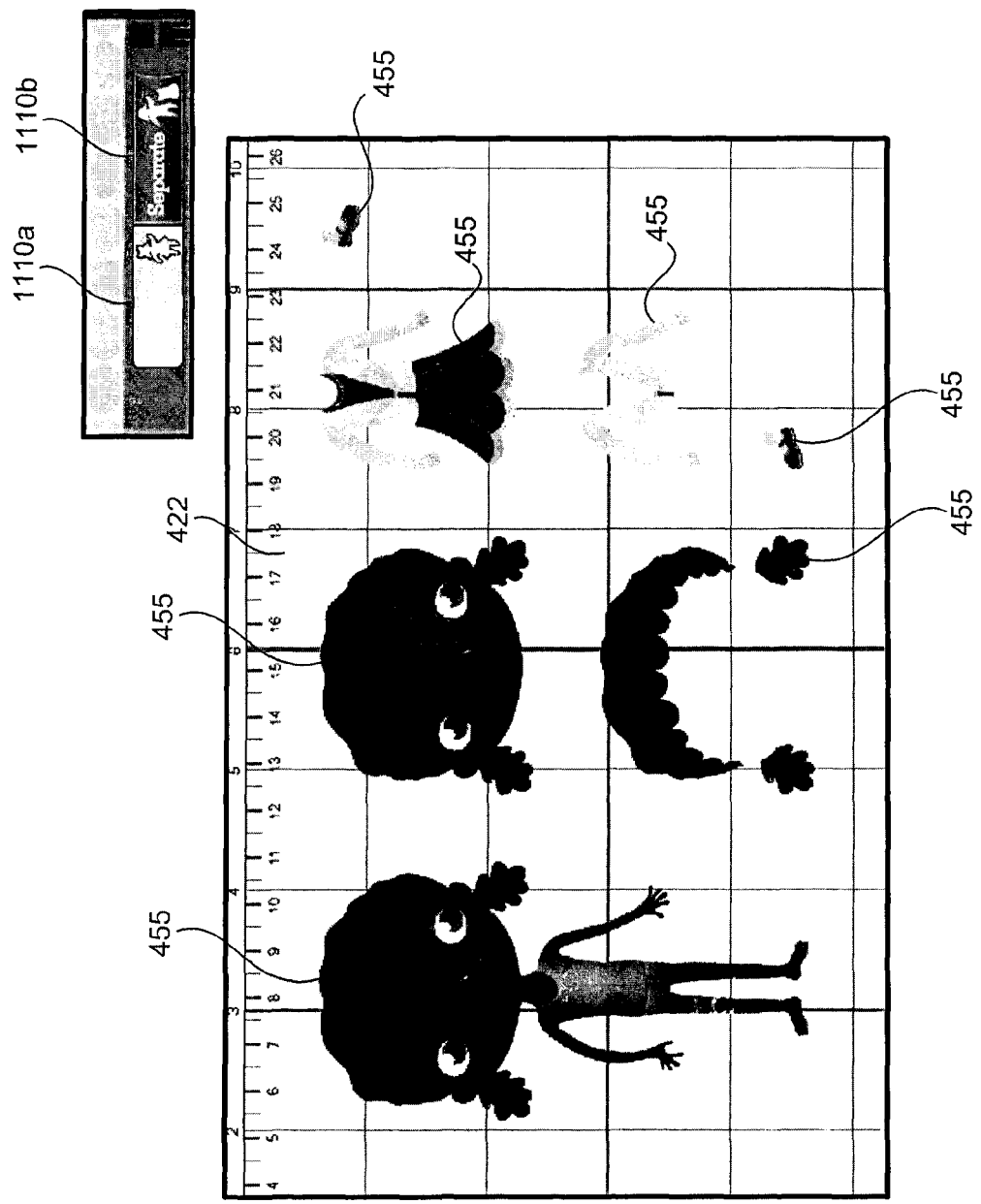
FIG. 11B is a schematic view of the image shown in FIG. 11A ungrouped or exploded into component images.

Referring to FIGS. 11A and 11B, in some implementations, the design software 100 allows the user to group and ungroup design objects 450 as well as edit the design objects 450 separately or while grouped. When selected, a design object 450 (grouped or ungrouped) may have an edit box 1100 displayed around it. The edit box 1100 may have handles for editing the design object 450. For example, a rotate handle 1102 can be manipulated by the user to alter a rotation of the design object 450 with respect to the X-axis or the Y-axis, a size handle 1104 can be manipulated by the user to alter a width or height of the design object 450 along the X-axis or the Y-axis, respectively. In the example show, the edit box includes an X-Y size handle 1104xy for alter both a width and height of the selected design object 450, an X-size handle 1104x for altering a width of the selected design object 450 along the X-axis, and a Y-size handle for altering a height of the selected design object 450 along the Y-axis. The edit box 110 may include an edit group button 1106 for grouping/ungrouping selected design objects 450 and applying edit changes to one or more selected design objects 450.

The user may group or combine design objects 450 by selecting a combine button 1110a. An exemplary grouped design object 450 is shown in FIG. 11A. While grouped, any edits to the grouped design object 450 can be applied to the constituent design objects 450. Similarly, the user may ungroup grouped design objects 450 (e.g. exploding a composite image) by selecting a separate button 1110b. An exemplary grouped design object 450 is shown in FIG. 11B. The user may edit or manipulate the individual design objects 450 and then regroup the design objects 450 by selecting the combine button 1110a.

In some examples the edit group button 1106 appears when a design object 450 (e.g., an image or glyph 455) is selected which is either a group of other design objects 450 or has composite layers that can be separated. Selecting the edit group button activate an edit group mode. Once in this mode, selecting the separate button 1110b causes all of parts of a grouped or composite glyph 455 to explode or separate into individual glyphs 455. Selecting the combine button 1110a can place the individual glyphs 455 back into a composite group again. Individual glyphs 455 can be edited further (e.g., scaled, rotated, mirrored, contoured, etc.). If the user transforms individual glyphs 455, the separate button 1110b may become disabled or hidden, while the combine button 1110a is enabled. If the user selects the combine button 1110a, the individual glyphs 455 may revert back to their original state, without transformations. However, this may not apply to fills. If a user ungroups the composite glyph 455 and re-arranges the individual ungrouped child glyphs 455 before re-grouping them, the alterations may change what defines where the child glyphs 455 are set inside of the composite glyph 455. The separate and combine functionality may use that new arrangement to determine how to combine the glyphs 455 back together into a grouped or composite glyph 455. In some examples, if some glyphs 455 have been grouped together without overlapping each other, the separate button may not be enabled. Moreover, the user can execute a cut command on the electronic cutting machine 150 to cut the project with glyphs 455 in either a grouped/composite state or an ungrouped/exploded state.

Figure 12A:
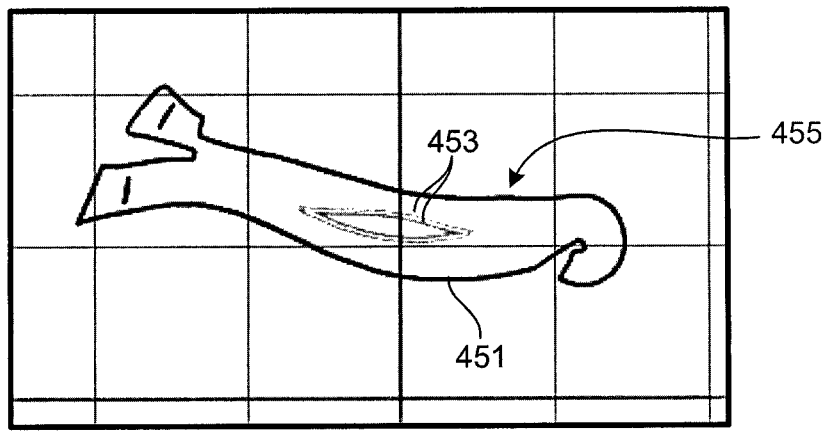
FIGS. 12A-12C are schematic views of a design object have contours or cut paths that can be hidden or disabled.
Figure 12B:
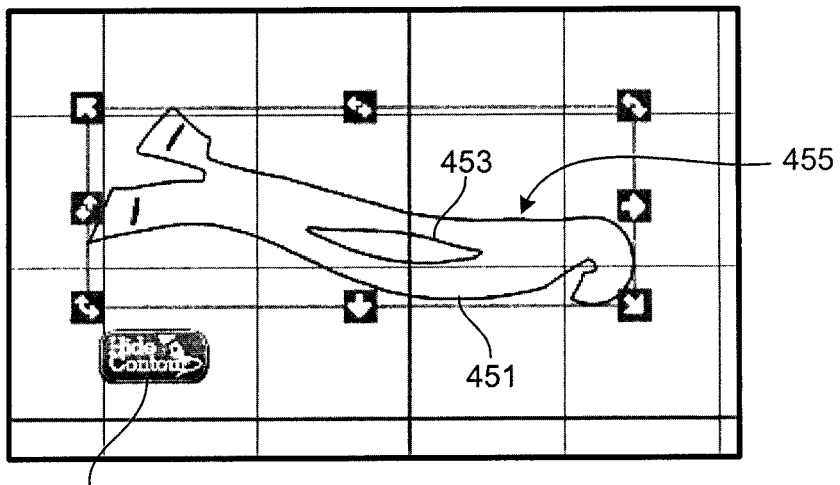
Figure 12C:
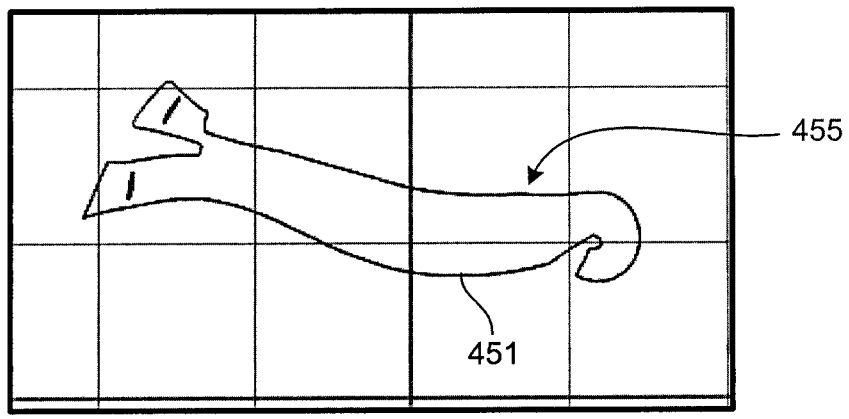

Referring to FIGS. 12A-12C, in some examples, when a user selects a glyph 455, a hide contours button 1210 may appear on the glyph 455. Selection of the hide contours button 710 activates a hide contours mode where the user can select cut paths 453 to be hidden or disabled. The user may hide cut paths 453 or reveal/enable individual hidden cut paths 453 in this mode (e.g., by clicking on the respective cut path 453 to toggle between hidden and unhidden). For example, in the examples shown in FIGS. 12A and 12B, the use has hidden a selected cut path 453 in an interior of the glyph 455. Moreover, the user can execute these commands on individual or grouped/composite glyphs 455. The hidden or disabled cut paths 453 are not cut by the electronic cutting machine 150. To exit the hide contours mode, the user may press an exit button or escape key (<ESC>) (not shown). The hide contours button 1210 may not appear over a glyph 455, if the glyph 455 has no contours or cut paths within an outline cut path 451 or no cut paths 453 can be hidden or disabled, as in the example shown in FIG. 12C.

Figure 13A:
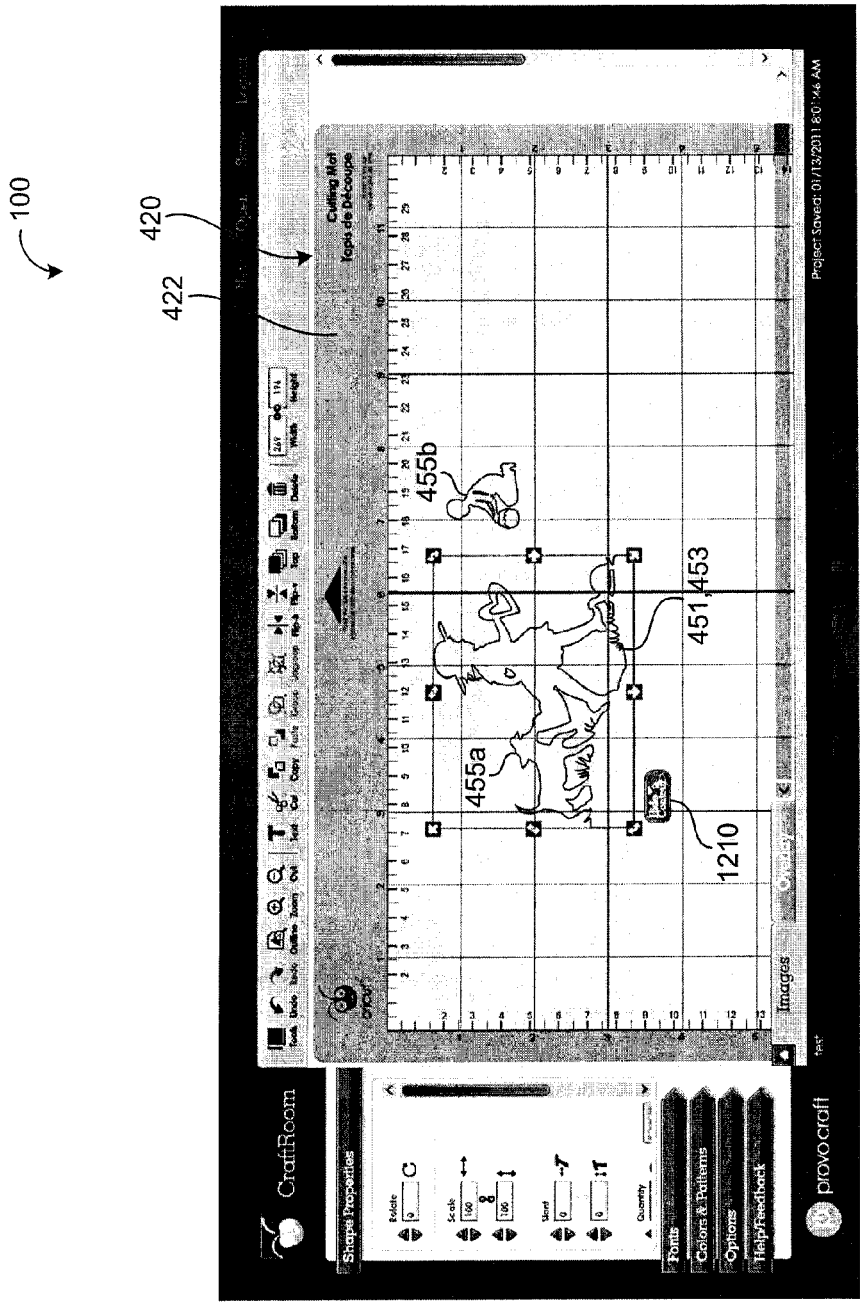
FIGS. 13A and 13B are schematic views of first and second design objects brought together for welding.
Figure 13B:
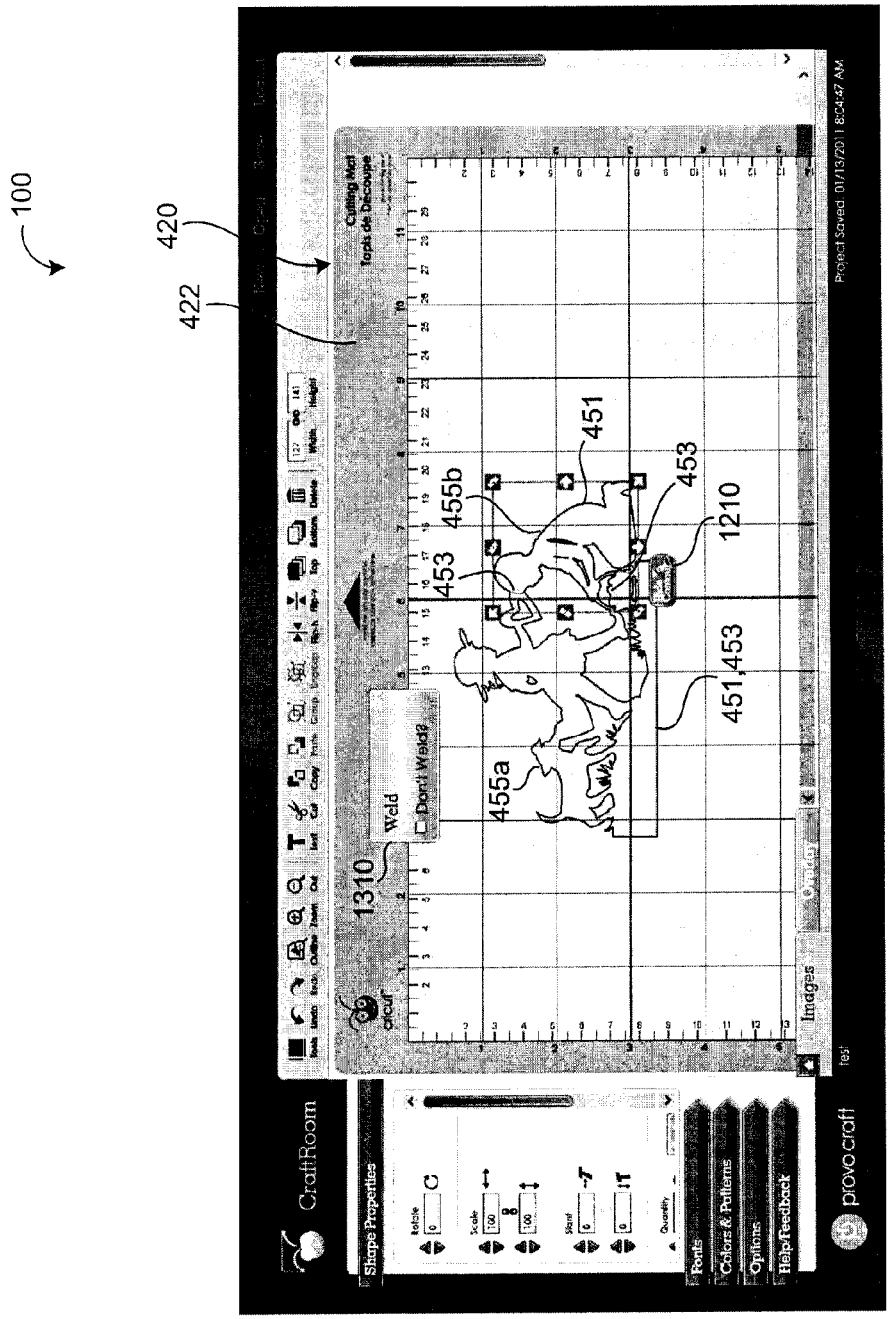

Referring to FIGS. 13A and 13B, in some examples, when first and second glyphs 455a, 455b are placed on the virtual mat 422 and moved to positions that intersect each other, the user may be prompted by the design software 100 to elect whether to have the first and second glyphs 455a, 455b automatically welded or joined together as a combined glyph 455. In the example shown, the design software 100 determines if the first and second glyphs 455a, 455b are touching or otherwise intersecting and if so, then displays a weld election prompt 1310 to receive a user selection to keep the intersecting glyphs 455a, 455b separate or to join them together.

In the example shown in FIG. 13B, the displays the hide contours button 1210 on or near the selected second glyph 455b. The user can select hideable cut paths 453 of the second glyph 455b and/or the welded glyphs 455a, 455b to hide or disable those cut paths 453 from being cut on the electronic cutting machine 150.

Figure 14A:
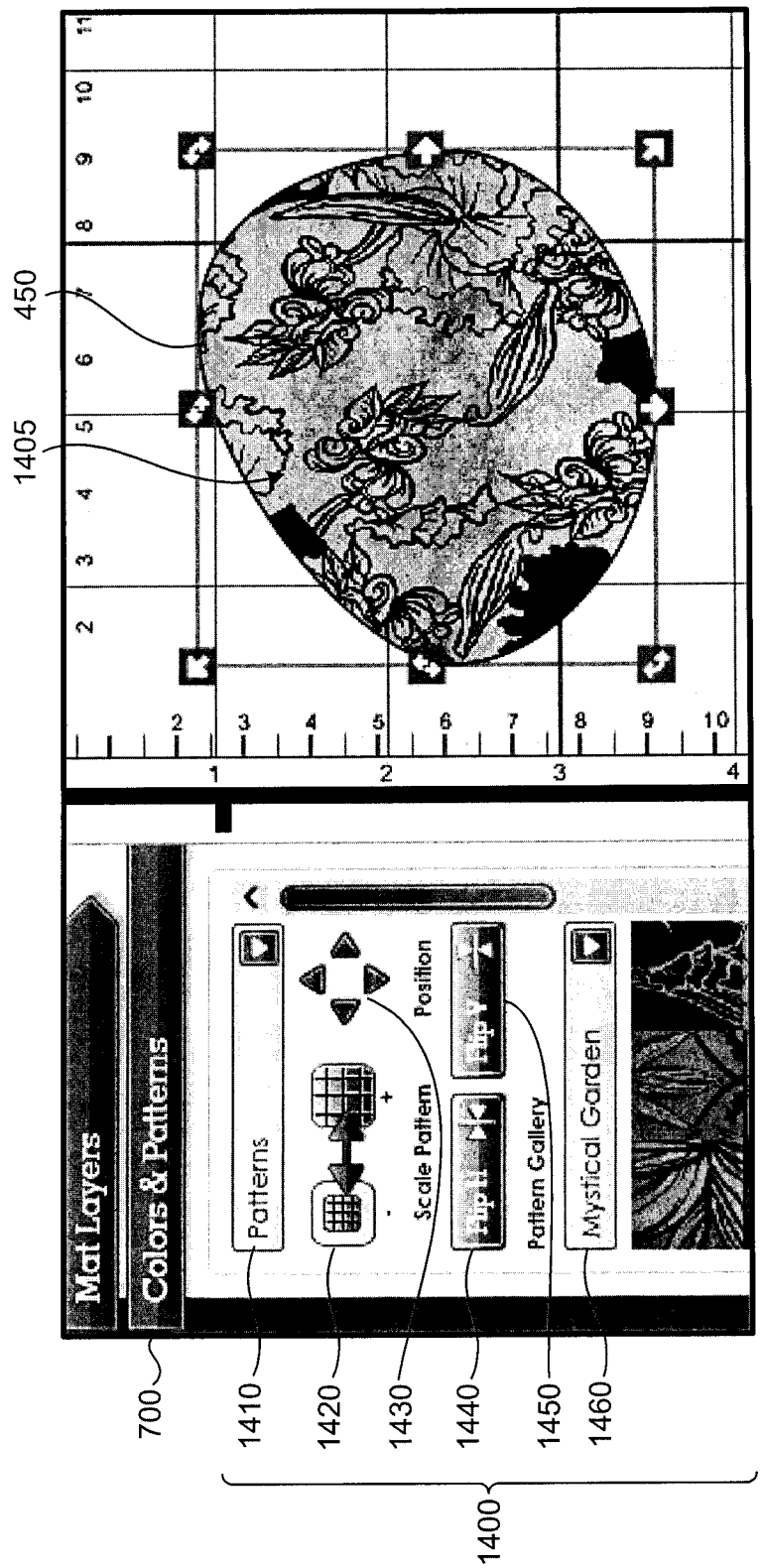
FIGS. 14A-14C are schematic views of patterns control on a design view for altering a pattern of a selected design object.
Figure 14B:
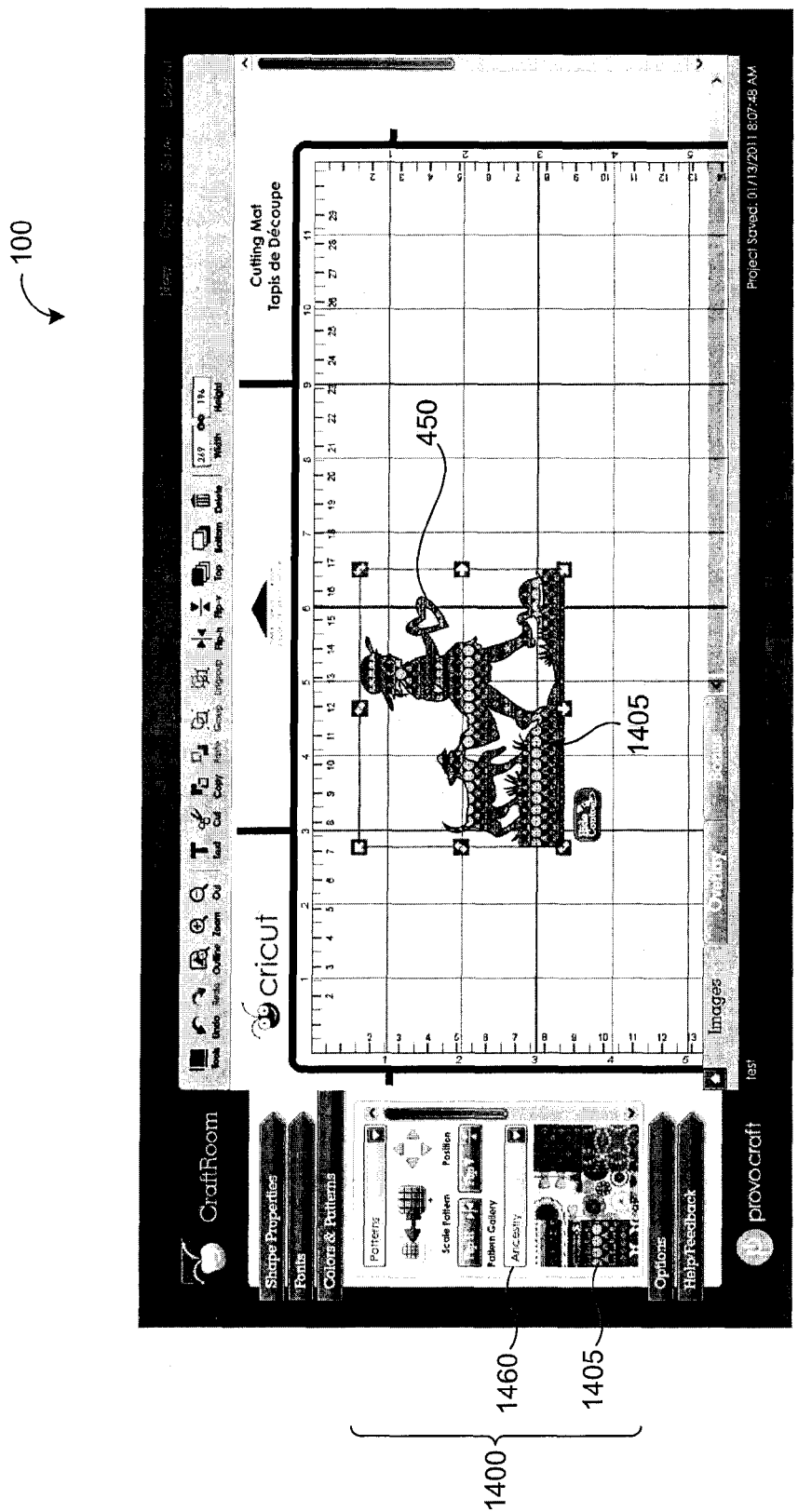
Figure 14C:
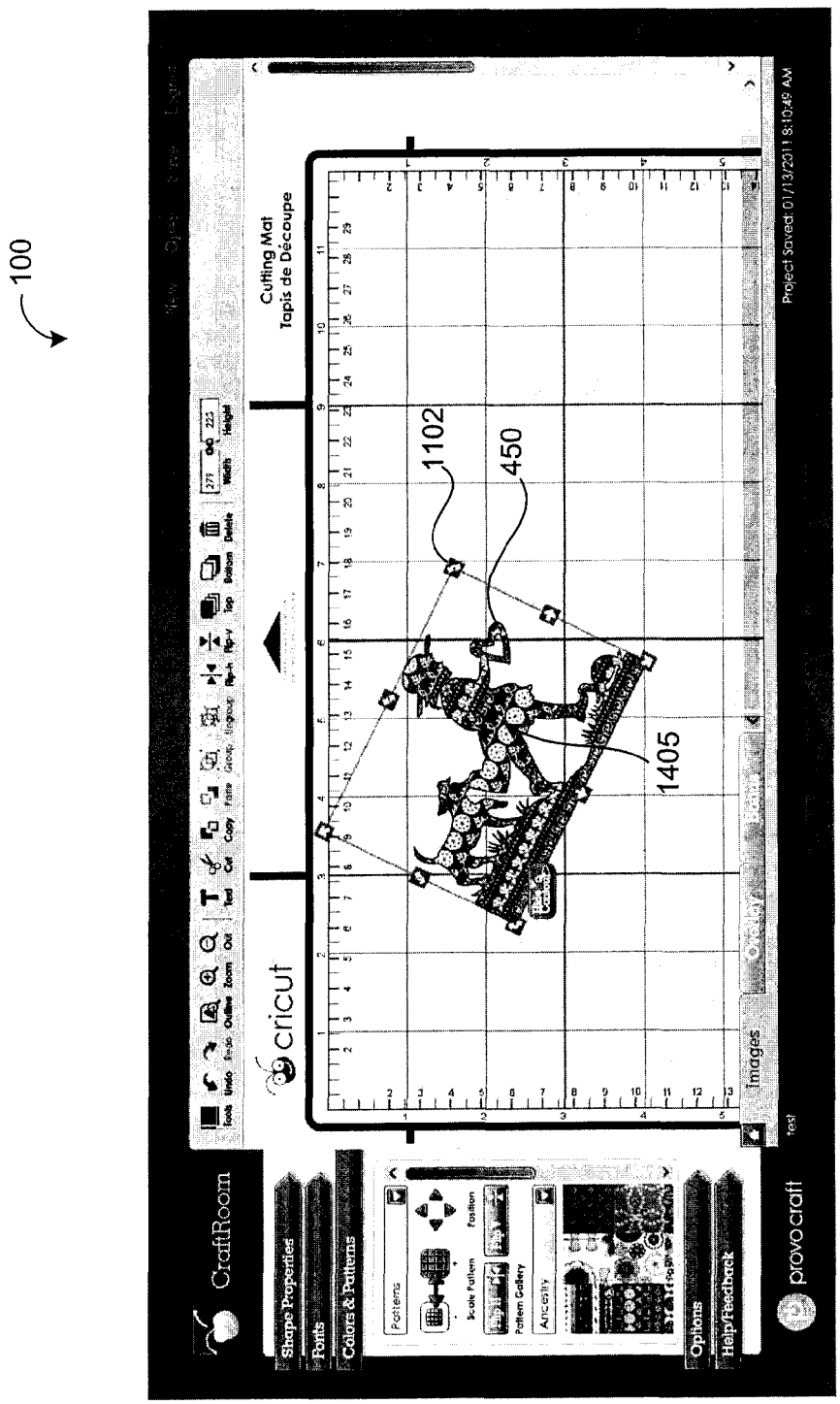

Referring to FIGS. 14A-14C, in some implementations, the colors palette 700 includes a patterns control 1400 for editing a pattern of a selected design object 450 or glyph 455. The patterns control 1400 may include a pattern selector 1410 (e.g., a drop down list) for selecting a pattern 1405 to apply to a selected design object 450, a pattern scale command 1420 for altering a size of a pattern 1405, a pattern position command 1430 for altering a pattern position, a horizontal flip command 1440 for flipping a pattern 1405 about a Y-axis, and a vertical flip command 1450 for flipping a pattern 1405 about an X-axis. The scale pattern command 1420 can be configured to magnify an appearance of the pattern 1405 or alter a distance between repeating features of the pattern 1405 within the selected design object 450. In the example shown in FIG. 14B, the user may select a pattern 1405 from a pattern gallery 1460 to apply the selected pattern 1405 to a selected design object 450. FIG. 14C illustrates how the user may rotate the design object using the rotate handle 1102, which in turn rotates the pattern 1405 applied to the design object. The design object 450 may be a container that holds the pattern 1405, such that edits or alterations applied to the container affect the contents of the container.

Figure 15:
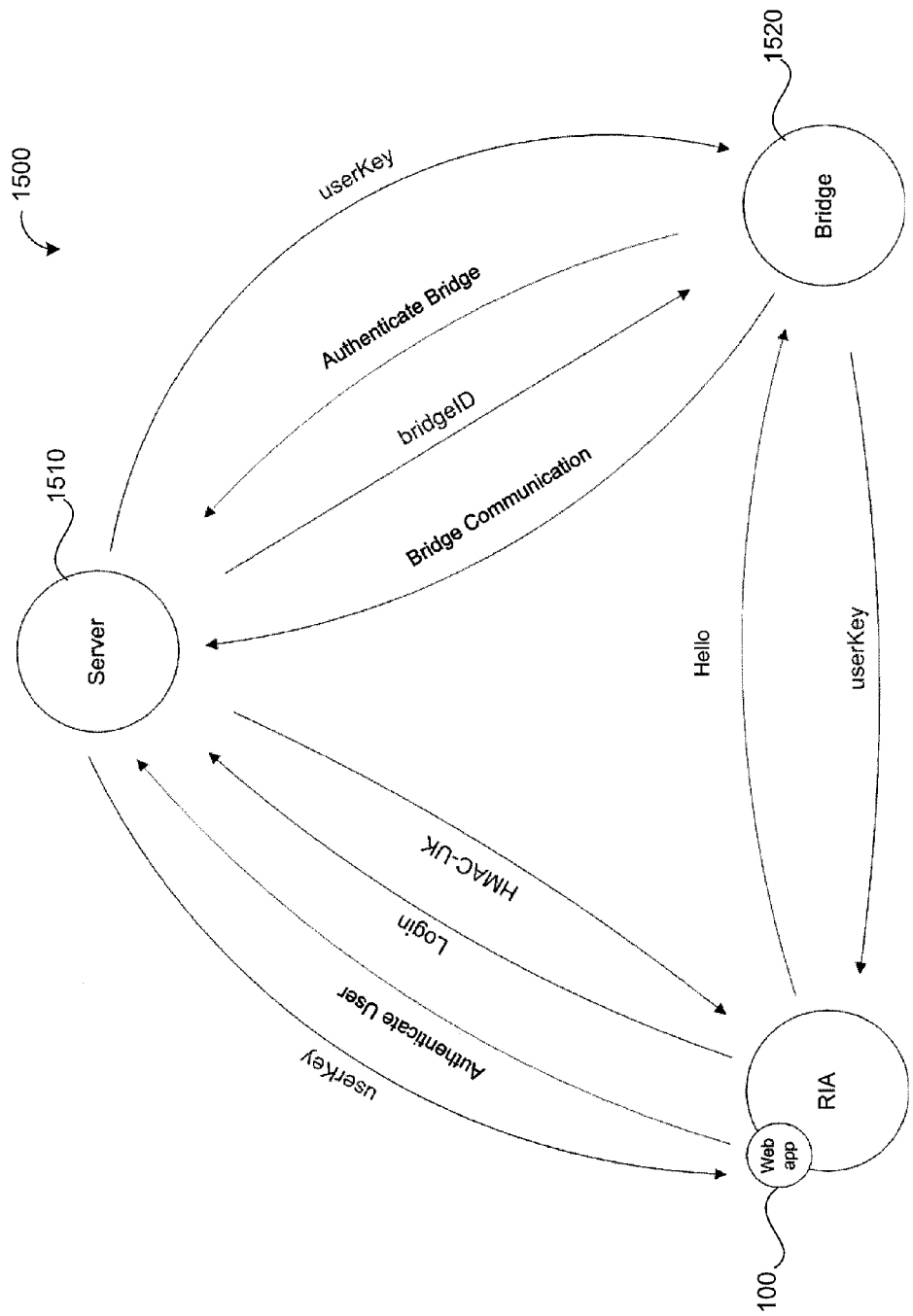
FIG. 15 is a schematic view of a security architecture for a rich interne application and an electronic cutting machine.

FIG. 15 provides a schematic view of a security architecture 1500 for the design software 100. Each cartridge 140 can be encrypted using the Advanced Encryption Standard (AES), which is a symmetric-key encryption standard having three block ciphers, AES-128, AES-192 and AES-25. Each of these ciphers has a 128-bit block size, with key sizes of 128, 192 and 256 bits, respectively. When a user requests information or content from the cartridge 140, the design software 100 may decrypt the information or content of the cartridge 140 with an AES session key and then decipher an AES cartridge key, which can be used to decrypt cartridge content. In the example shown, the design software 100 (e.g., a rich internet application) sends login credentials to a server 1510, which collects an internet protocol (IP) address, generates a unique hash-based message authentication code (HMAC) for the user, creates a user session key, and returns the HMAC to the design software 100 optionally with user information stored on the server 1510. The design software 100 sends an authenticate user request to the server 1510, which includes an encrypted authentication object that uses at least a portion of the returned HMAC. The server decrypts the authentication object, verifies information of the authentication object as well as the IP address and returns the user session key. The design software 100 uses the user session key to access content of the cartridges 140. All communications with the server 1510 can be via a secure socket layer (SSL). The server 1510 may be a cloud computing server.

The electronic cutting machine 150 includes a bridge 1520, which provides a communication gateway between the electronic cutting machine 150 (e.g., a controller, motors, actuators, etc.) and the server 1510 and/or the design software 100. To establish communication with the electronic cutting machine 150, the design software 100 sends a hello message to the electronic cutting machine 150 that includes at least a portion of the HMAC. The electronic cutting machine 150 sends an encrypted bridge communication to the server 1510. The server decrypts and validates the bridge communication. If the bridge communication is valid, the server 1510 returns a bridge identification (ID). The bridge 1520 sends an authenticate bridge request to the server 1510, which includes an encrypted authentication object that uses at least a portion of the HMAC. The server decrypts the authentication object, verifies the associated IP address and returns a user key. The bridge 1520 may return the user key to the design software 100 for authenticating and/or decrypting communications therebetween. If the server fails to received further communications from the design software 100 and/or the bridge 1520, the server 1510 destroys the user keys, thus disabling communications between the design software 100, the server 1510, and/or the bridge 1520.

Figure 16:
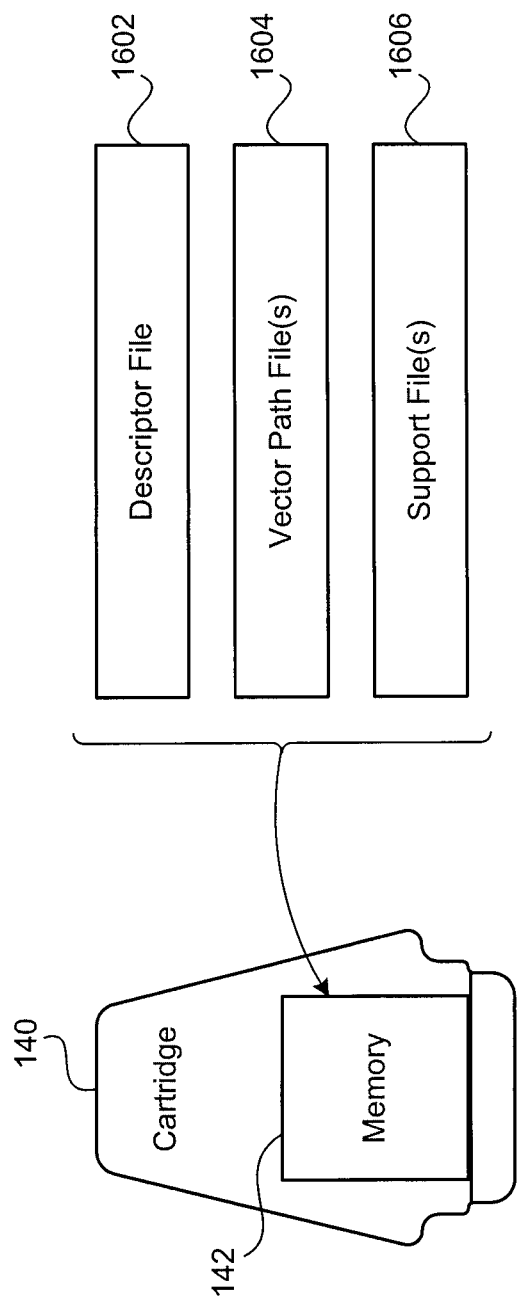
FIG. 16 is a schematic view of a cartridge and information stored thereon.

Referring to FIGS. 1 and 16, the cartridge 140 may store information (e.g., in memory 142) in a manner that allows delivery of collections of artwork printable and/or cuttable on the electronic cutting machine 150. The information may be AES encrypted. The cartridge 140 may store a descriptor file 1602, one or more vector path files 1604 (e.g., glyphs 455), and optionally one or more supporting files 1606 (e.g., image and/or FXG vector format files).

The descriptor file 1602 may have an extensible markup language (XML) format that includes information (e.g., tagged information) on the vector path file(s) 1604, organization of multiple vector path files 1604, etc. For example, the descriptor file 1602 may have XML tags for glyphs 455, corresponding fonts, keyboard mappings, special cutting instructions, and glyph groupings (e.g., composite glyphs 455). Exemplary tags are shown in table 1.

TABLE 1

| Tag | Description |
| --- | --- |
| Name | Name of cartridge package |
| ID | Unique identification number for the cartridge |
| Version | Cartridge version |
| Type | Electronic cutting machine types or models that the cartridge may be used on |
| Fonts | Fonts used in the collections of artwork |
| Glyphs | Provides definitions all top-level glyphs belonging to each font, key-mappings, and other font-supporting features Each glyphs may have a <children> list of child glyphs to form a composite glyph |
| Child Glyphs | Provides definitions of children glyphs of a parent glyph |
| Fills | References to fills |
| Color Palette | A swatch library for solid-color fills |

In some implementations, fonts are collections of glyphs 455 accessible via a keyboard. Fonts may each contain multiple glyphs 455 (e.g., up to 50 glyphs) organized in a 10×10 array, and optionally assigned Unicode values. Each font may include: an identification attribute, which can be a unique ID used by a glyph 455 to reference the font it belongs to; a feature attribute, which may provide an order by which the fonts are organized or grouped; and a font-family attribute, which may be a name of the font as displayed by the design software 100.

Glyphs 455 may define a piece of artwork associated with a font or with another glyph 455 (in the case of composite glyphs 455). Each glyph 455 may include a glyph definition accessible from the descriptor file 1602. The glyph definition may provide attributes such as a glyph identification number, name, type (e.g., shape or categorical descriptor), a key row and column (e.g., a position of the glyph 455 on a 10×10 key array displayed by the design software 100 or provided on the electronic cutting machine 150), an associate font, a cut and/or print mode, etc. The cut mode may include a normal cut mode (e.g., cutting directly on the cut path) and an offset cut mode (e.g., cutting parallel to a cut path at an offset distance, so as to provide a margin around the glyph 455). Each glyph 455 may include a cut path file providing cut path coordinates and a fill file. The fill file may be referenced in cut path glyph file and provides images (e.g., pngs or jpgs) or FXG artwork. For child glyphs 455, the glyph definition may include positioning information relative to a corresponding parent glyph 455 and/or other child glyphs 455.

The fill file may include attributes such as a background bleed color (e.g., a hexadecimal value) used for printing a bleed or margin color around the glyph 455. The design software 100 may provide (automatically or upon user selection) a buffer region around the glyph 455 upon execution of a cut command or the user may select a bleed boundary command to create the buffer region around the glyph 455. The buffer region allows cutting the glyph 455 along its perimeter while maintaining any coloration (e.g., via printing) of glyph 455 completely up to the cut perimeter. The buffer region may have a threshold thickness that stays constant or is not exceeded (e.g., maximum or minimum) when the glyph 455 is scaled or altered. In some implementations, the buffer region is created by extrapolating colors outwardly beyond the image perimeter. For example, pixel colors may be propagated a threshold number of pixels outwardly form the image perimeter and overlapping colors mixed appropriately (e.g., according to a mixing criteria, such red+blue=purple). The glyph definition may include an offset attribute defining the offset distance and/or a maximum offset attribute defining a maximum offset distance allowed for the glyph 455. Other fill attributes may include a fill mode, which may indicate whether a fill is scaled or repeated to fill a space, and transform, which may indicate whether an image of the fill can be scaled by dots per inch (DPI) or at another resolution.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

Implementations of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal, that is generated to encode information for transmission to suitable receiver apparatus.

A computer program (also known as a program, software, software application, script, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio player, a Global Positioning System (GPS) receiver, to name just a few. Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described is this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular implementations of the invention. Certain features that are described in this specification in the context of separate implementations can also be implemented in combination in a single implementation. Conversely, various features that are described in the context of a single implementation can also be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multi-tasking and parallel processing may be advantageous.

Moreover, the separation of various system components in the embodiments described above should not be understood as requiring such separation in all embodiments, and it should be understood that the described program components and systems can generally be integrated together in a single software product or packaged into multiple software products.

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. A method of communication with a server, the method comprising:
    receiving a login request from an internet application;
    producing a hash-based message authentication code;
    producing a user session key;
    returning the hash-based message authentication code to the internet application;
    receiving an authenticate user request from the internet application;
    returning the user session key to the internet application;
    receiving a bridge communication from an electronic cutting machine bridge;
    returning a bridge identification to the electronic cutting machine bridge;
    receiving an authenticate bridge request from the electronic cutting machine bridge;
    returning a user bridge key to the electronic cutting machine bridge;
    and receiving at the internet application the user bridge key from the electronic cutting machine bridge.

2. The method of claim 1, wherein at least one of the login request and the authenticate user request from the internet application is encrypted.

3. The method of claim 2, further comprising decrypting at least one of the login request and the authenticate user request.

4. The method of claim 1, wherein at least one of the bridge communication and the authenticate bridge request from the electronic cutting machine bridge is encrypted.

5. The method of claim 4, further comprising decrypting at least one of the bridge communication and the authenticate bridge request.

6. The method of claim 1, wherein, prior to the receiving at the server the bridge communication from the electronic cutting machine bridge step, further comprising establishing communication between the electronic cutting machine and the internet application by sending a hello message that includes at least a portion of the hash-based message authentication code.

7. The method of claim 1, wherein, after the returning the user bridge key to the electronic cutting machine bridge from the server step, if the server fails to receive further communication from the internet application or the electronic cutting machine bridge, further comprising utilizing the server for destroying the user session key and the user bridge key.

8. An electronic cutting machine system comprising:
    an internet application;
    a server in communication with the internet application, the server receiving a login request from an internet application and producing a hash-based message authentication code and a user session key, the server returning the hash-based message authentication code to the internet application, the server receiving an authenticate user request from the internet application and returning the user session key to the internet application;
    and an electronic cutting machine having a bridge in communication with the internet application and the server;
    wherein the server receives a bridge communication from an electronic cutting machine bridge and returns a bridge identification to the electronic cutting machine bridge, the server receiving an authenticate bridge request from the electronic cutting machine bridge and returning a user bridge key to the electronic cutting machine bridge;
    and wherein the internet application receives the user bridge key from the electronic cutting machine bridge.

9. A method of communication with a server, the method comprising:
    interfacing a content cartridge with an electronic cutting machine including an electronic cutting machine bridge;
    decrypting content stored on the content cartridge by:
    receiving a login request from an internet application, producing a hash-based message authentication code, producing a user session key, returning the hash-based message authentication code to the internet application, receiving an authenticate user request from the internet application, returning the user session key to the internet application for accessing the content stored on the content cartridge;

receiving at the server a bridge communication from the electronic cutting machine bridge;

returning a bridge identification to the electronic cutting machine bridge from the server;

receiving at the server an authenticate bridge request from the electronic cutting machine bridge;

and returning a user bridge key to the electronic cutting machine bridge from the server.

10. The method of claim 9, wherein at least one of the login request and the authenticate user request from the internet application is encrypted.

11. The method of claim 10, further comprising decrypting at least one of the login request and the authenticate user request.

12. The method of claim 9, wherein at least one of the bridge communication and the authenticate bridge request from the electronic cutting machine bridge is encrypted.

13. The method of claim 12, further comprising decrypting at least one of the bridge communication and the authenticate bridge request.

14. The method of claim 9, further comprising receiving at the internet application the user bridge key from the electronic cutting machine bridge.

15. The method of claim 9, wherein, prior to the receiving at the server the bridge communication from the electronic cutting machine bridge step, further comprising establishing communication between the electronic cutting machine and the internet application by sending a hello message that includes at least a portion of the hash-based message authentication code.

16. The method of claim 9, wherein, after the returning the user bridge key to the electronic cutting machine bridge from the server step, if the server fails to receive further communication from the internet application or the electronic cutting machine bridge, further comprising utilizing the server for destroying the user session key and the user bridge key.

* * * * *